United States Patent
Frymark et al.

(10) Patent No.: US 10,433,941 B2
(45) Date of Patent: Oct. 8, 2019

(54) DENTAL SOLUTION DISPENSER AND METHODS OF USE

(71) Applicant: Young Microbrush, LLC, Grafton, WI (US)

(72) Inventors: John Frymark, Chicago, IL (US); Todd Korup, Port Washington, WI (US); Donald Melnikoff, Mukwonago, WI (US); Michael Nix, Port Washington, WI (US); Robert E. Kreutzer, Jr., Columbia, IL (US); Richard Gaggioli, Milwaukee, WI (US); Wayne Siebrecht, Golden, CO (US); Scott Rote, Mokena, IL (US); Aaron B. Eiger, Chicago, IL (US); Nathan Wicker, Forest Park, IL (US); Kent Solberg, Whitefish Bay, WI (US)

(73) Assignee: YOUNG MICROBRUSH, LLC, Grafton, WI (US)

(*) Notice: Subject to any disclaimer, the term of this patent is extended or adjusted under 35 U.S.C. 154(b) by 218 days.

(21) Appl. No.: 15/148,484

(22) Filed: May 6, 2016

(65) Prior Publication Data

US 2016/0324608 A1 Nov. 10, 2016

Related U.S. Application Data

(60) Provisional application No. 62/157,624, filed on May 6, 2015, provisional application No. 62/268,897, filed on Dec. 17, 2015.

(51) Int. Cl.
*A61C 19/06* (2006.01)
*A46B 11/00* (2006.01)
(Continued)

(52) U.S. Cl.
CPC ........ *A61C 19/063* (2013.01); *A46B 11/0024* (2013.01); *A46B 11/0037* (2013.01);
(Continued)

(58) Field of Classification Search
CPC .... A61C 5/62; A61C 5/50; A61C 5/66; A61C 3/005; A61C 19/063; A61C 17/227;
(Continued)

(56) References Cited

U.S. PATENT DOCUMENTS 4,269,207 A * 5/1981 Konrad ............... A46B 9/04
132/308
4,530,369 A * 7/1985 Adams ............... A45D 40/04
132/311
(Continued)

FOREIGN PATENT DOCUMENTS

EP 0746993 A1 12/1996
WO 85-04646 A1 10/1985

OTHER PUBLICATIONS

International Search Report and Written Opinion received in corresponding PCT Application No. PCT/US2016/031215, dated Aug. 16, 2016.

*Primary Examiner* — Wade Miles
*Assistant Examiner* — Matthew P Saunders
(74) *Attorney, Agent, or Firm* — McDermott Will & Emery

(57) ABSTRACT

A dental solution dispenser includes a body having a first end, a second end, and including a front housing at the first end, a twist back at the second end, and a grip that interposes the front housing and the twist back. An applicator tip is coupled to the body at the first end, and an ampoule assembly is positioned within the body and includes an ampoule sealed at one end with a frangible seal and defining a fluid chamber for storing a dental solution. A mandrel
(Continued)

extends longitudinally within the body and provides a piercing member. The twist back is rotatable relative to the grip to pierce the frangible seal with the piercing member. A trigger is coupled to the body and pivotable between an engaged position, where the trigger engages the ampoule assembly, and a disengaged position, where the trigger disengages the ampoule assembly.

24 Claims, 13 Drawing Sheets

(51) Int. Cl.
    *A61C 3/00*     (2006.01)
    *A61C 5/62*     (2017.01)
(52) U.S. Cl.
    CPC .......... *A46B 11/0065* (2013.01); *A61C 3/005* (2013.01); *A61C 5/62* (2017.02)
(58) Field of Classification Search
    CPC ............ A46B 11/0024; A46B 11/0037; A46B 11/0065; A46B 2200/1066; A46B 11/00; A46B 11/0027; A46B 11/0031; A46B 11/0055; A46B 11/0006; A61M 5/20; A61M 5/24; A61M 5/3158; A61M 5/31553; A61M 5/31511; A61M 2005/2407
    USPC ...... 433/80–90, 216; 401/171, 191; 604/135
    See application file for complete search history.

(56) References Cited

U.S. PATENT DOCUMENTS

| | | | | |
|---|---|---|---|---|
| 5,172,807 | A * | 12/1992 | Dragan | A61C 5/64 |
| | | | | 206/219 |
| 6,056,466 | A | 5/2000 | Johnson et al. | |
| 6,206,600 | B1 * | 3/2001 | Rosenberg | A46B 5/00 |
| | | | | 401/153 |
| 6,729,789 | B2 * | 5/2004 | Gordon | A46B 11/0017 |
| | | | | 15/111 |
| 8,534,950 | B2 | 9/2013 | Sylvester | |
| 2008/0089733 | A1 * | 4/2008 | Lochak | A46B 11/0024 |
| | | | | 401/180 |
| 2014/0030004 | A1 * | 1/2014 | Nakamura | B05C 11/00 |
| | | | | 401/176 |

* cited by examiner

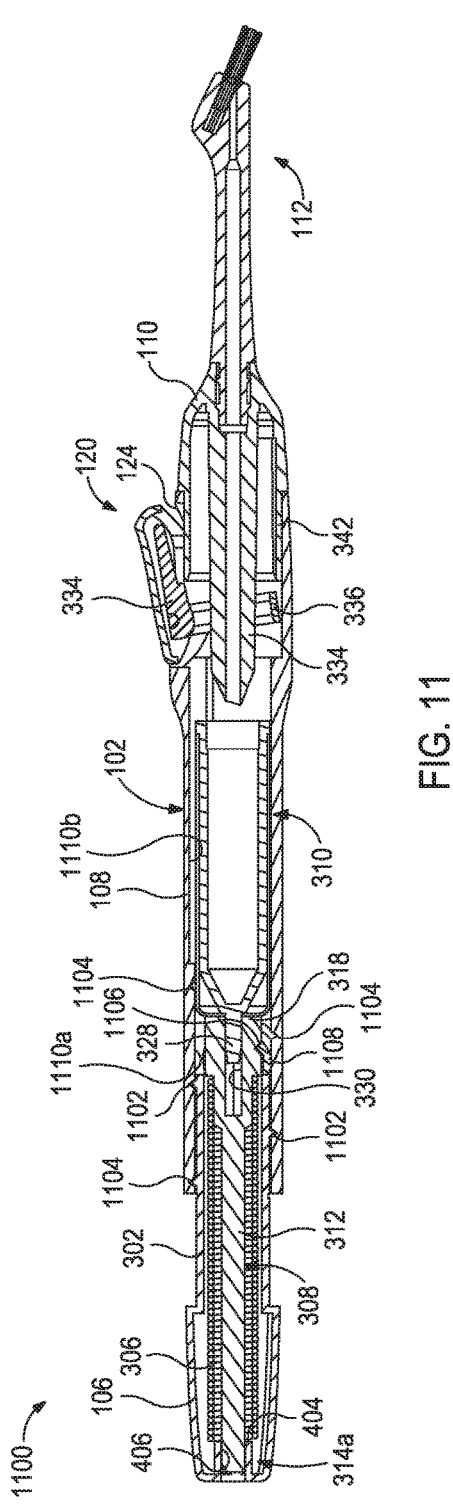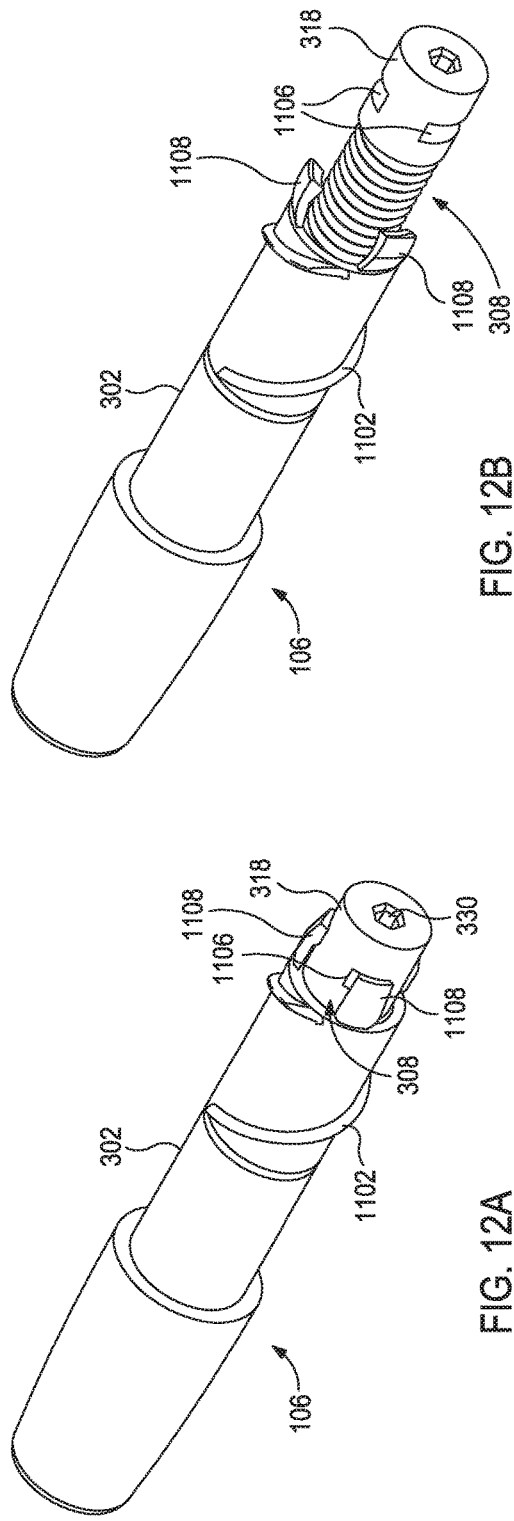
FIG. 11
FIG. 12A
FIG. 12B

DENTAL SOLUTION DISPENSER AND METHODS OF USE

CROSS-REFERENCE TO RELATED APPLICATIONS

This application is related to and claims priority to U.S. Provisional Patent App Ser. No. 62/157,624, which was filed on May 6, 2015, and U.S. Provisional Patent App Ser. No. 62/268,897, which was filed on Dec. 17, 2015.

BACKGROUND

In the field of dentistry, various dental medicaments and solutions are applied to a patient's teeth as part of routine dental cleaning, preparation, and restorative processes. During dental cleaning processes, for example, fluoride is often applied to teeth to prevent tooth decay since fluoride hardens the enamel tooth surface by forming calcium fluoride. One method of applying fluoride to teeth is by dispensing a fluoride gel composition into a dental tray and then positioning the dental tray over the teeth of the patient to immerse the teeth in the fluoride gel composition. The tray holds the fluoride gel composition adjacent to the teeth and, after a desired amount of time, the dental tray is removed and the remaining fluoride gel composition is then rinsed from the teeth.

Another method of applying fluoride to teeth involves the direct application of a fluoride varnish to the patient's teeth. Fluoride varnish typically includes a mixture of fluoride salt dispersed within a sticky, adhesive, hydrophobic varnish material. The fluoride varnish is usually stored within a dedicated cup or tray that can be accessed by the dental practitioner. The dental practitioner dips a brushed dental applicator (alternately referred to as a "dental brush") into the cup or tray and brushes the fluoride varnish onto the teeth. Once applied, the fluoride varnish adheres to the teeth and subsequently erodes away after several hours.

Today, various dental solution dispensers are available that include a brushed dental applicator used to deliver a dental solution to the teeth of a patient. Combination applicator and syringe dental solution dispensers, for example, often include an associated brushed dental applicator disposed on its end.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 11 is a cross-sectional side view of another example dental solution dispenser.

FIGS. 12A and 12B are isometric views of the twist back in engaged and disengaged positions, respectively, of the dental solution dispenser of FIG. 11.

DETAILED DESCRIPTION

The present disclosure relates to tools used in the field of dentistry and, more particularly, to dental solution dispensers used to deliver a dental solution to a tooth surface.

Figure 1:
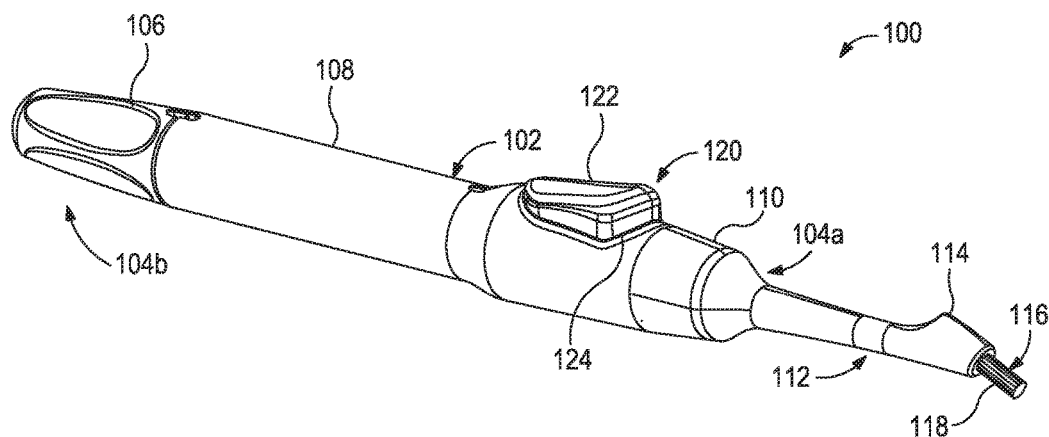
FIG. 1 is an isometric view of an exemplary dental solution dispenser.

FIG. 1 is an isometric view of an exemplary dental solution dispenser 100, according to one or more embodiments of the present disclosure. The dental solution dispenser 100 (hereafter "the dispenser 100") may be particularly useful in dispensing a dental solution as part of dental cleaning, preparation, and restorative processes. Dental solutions that may be applied using the dispenser 100 include any flowable dental composite, or any type of gel or paste that is commonly applied to teeth during any dental cleaning, preparation, or restorative process. Exemplary dental solutions that may be dispensed from the dispenser 100 include, but are not limited to, fluoride varnish, a flowable composite, a whitening solution, a whitening gel, a cement, an adhesive, a bonding agent, a desensitizer, an etchant, an any combination thereof.

As illustrated, the dispenser 100 may include a generally elongate body 102 having a first end 104a and a second end 104b. Two or more component parts of the dispenser 100 may be operatively coupled to form the body 102. For instance, the body 102 may comprise a twist back 106, a grip 108, and a front housing 110, where the twist back 106 is coupled to the grip 108, and the grip 108 is coupled to the front housing 110. Accordingly, the twist back 106, the grip 108, and the front housing 110 are collectively referred to herein as "the body 102." An applicator tip 112 may be coupled to the body 102 at the first end 104a and, more particularly, to the front housing 110.

A variety of coupling means may be employed to couple the twist back 106 to the grip 108, to couple the front housing 110 to the grip 108, and to couple the applicator tip 112 to the front housing 110. Suitable coupling means include, but are not limited to, a snap fit, a collet interface, one or more mechanical fasteners (e.g., screws, snap rings, pins, etc.), sonic welding, an adhesive, or any combination thereof. The body 102 and the applicator tip 112 may each be made of a plastic, such as polypropylene or another injection molded plastic, but could alternatively be made of other rigid materials, such as a metal, a composite material, or any combination of plastics, metals, and composite materials, without departing from the scope of the disclosure.

The applicator tip 112 includes a brush cup 114 that receives and otherwise houses a brush applicator 116 used to apply the dental solution directly to the teeth of a patient. The brush applicator 116 comprises a plurality of bristles 118 received within and secured to the brush cup 114. The bristles 118 may be made of natural and/or synthetic fibers or filaments that are reasonably soft so as not to irritate or damage target dental surfaces. Suitable natural fibers include, but are not limited to, cotton fibers, celluloses, gums, carbopolymers, water-dispersible polymers, and any combination thereof. Suitable synthetic fibers can include, but are not limited to, nylon, polyester, a polyamide, a polyolefin, a polypropylene, polyvinylpyrrolidone, and any combination thereof. In at least one embodiment, the bristles 118 may be made of extruded nylon fibers, such as TYNEX® nylon filaments commercially available through E. I. du Pont de Nemours and Company. In addition, the bristles 118 may be made from various injection moldable plastics formed using standard injection molding techniques, or may alternatively be formed through known flocking methods, such as electrostatic flocking or gravity flocking.

The dispenser 100 may further include a trigger 120 pivotably coupled to the body 102 at an intermediate location between the first and second ends 104a,b. As illustrated, the trigger 120 extends at least partially into the interior of the body 102 via an aperture 124 defined in the grip 108. The trigger 120 may include a trigger cap 122 that either forms an integral part of the trigger 120 or is secured (i.e., mechanically coupled, bonded, heat welded, sonic welded, etc.) to the trigger 120 for manual manipulation.

As described below, the trigger 120 may be configured to transition or "pivot" between an engaged position and a disengaged position. In the engaged position, the trigger 120 binds against one or more internal components of the dispenser 100 to prevent (or halt) discharge of the dental solution from the dispenser 100. In the disengaged position, the trigger 120 releases the internal component(s) and thereby allows the dispenser 100 to dispense the dental solution. A user may be able to manually manipulate the trigger 120 between the engaged and disengaged positions by engaging (i.e., pressing down on) the trigger cap 122. In some embodiments, the trigger 120 may be spring loaded and exhibit a natural tendency to remain in the engaged position. In other embodiments, however, the user may be required to manually move the trigger 120 back and forth between the disengaged and engaged positions.

Figure 2A:
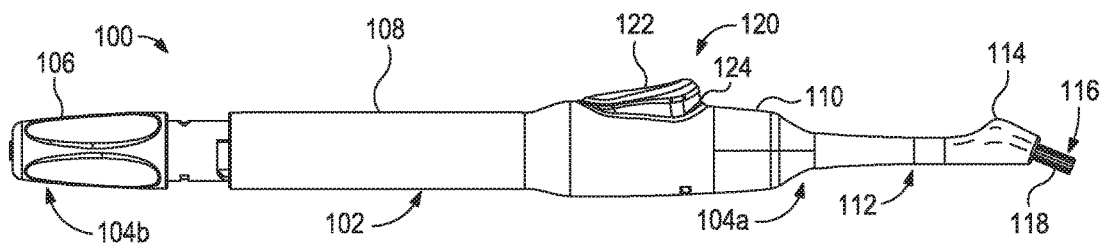
FIGS. 2A and 2B are side views of the dental solution dispenser of FIG. 1 in a loaded configuration and a primed configuration, respectively.
Figure 2B:
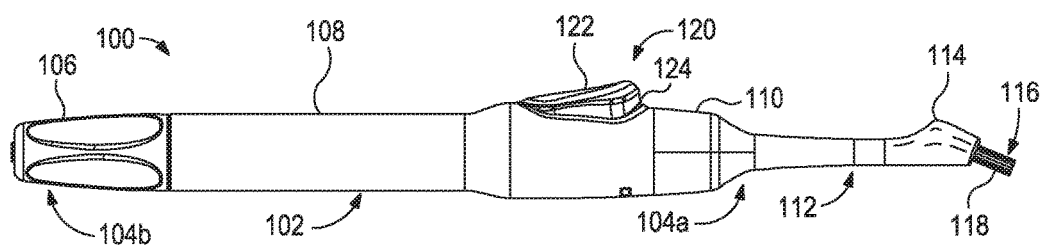

FIGS. 2A and 2B are side views of the dispenser 100 in a loaded configuration and a primed configuration, respectively, according to one or more embodiments. The dispenser 100 may be packaged and shipped to an end user for use while in the loaded configuration. Moving the dispenser 100 to the primed configuration requires manual manipulation provided by the user. Once the user manually transitions the dispenser 100 to the primed configuration, the dispenser 100 is then ready to selectively dispense the dental solution as desired by manipulating the trigger 120.

Briefly, and as will be described in more detail below, to move the dispenser 100 from the loaded configuration (FIG. 2A) to the primed configuration (FIG. 2B), a user manually grips and angularly rotates the twist back 106 relative to the grip 108 about the longitudinal axis of the body 102. Depending on the design configuration of the dispenser 100, the twist back 106 may be rotated either clockwise or counterclockwise with respect to the grip 108. Rotating the twist back 106 relative to the grip 108 progressively draws the twist back 106 into the interior of the grip 108 and causes an ampoule (not shown) movably positioned within the grip 108 to be penetrated to access a dental solution contained in the ampoule. With the ampoule penetrated, the dispenser 100 is then "primed" and otherwise ready to dispense the dental solution as desired. In some cases, dispensing the dental solution may be accomplished by manually pressing down on the trigger 120 to disengage the trigger 120 from internal components within the dispenser 100 and thereby allow the ampoule to move axially within the body 102. As the ampoule moves, the dental solution stored within the ampoule will be conveyed to the applicator tip 112 to be discharged (expressed) from the dispenser 100 at the brush applicator 116. Moving the trigger 120 back to the engaged position stops movement of the ampoule and thereby stops the discharge of the dental solution. In some cases, the trigger 120 naturally moves back to the engaged position once the user releases contact. In other cases, however, the user may be required to manually move the trigger 120 back to the engaged position.

Figure 3:
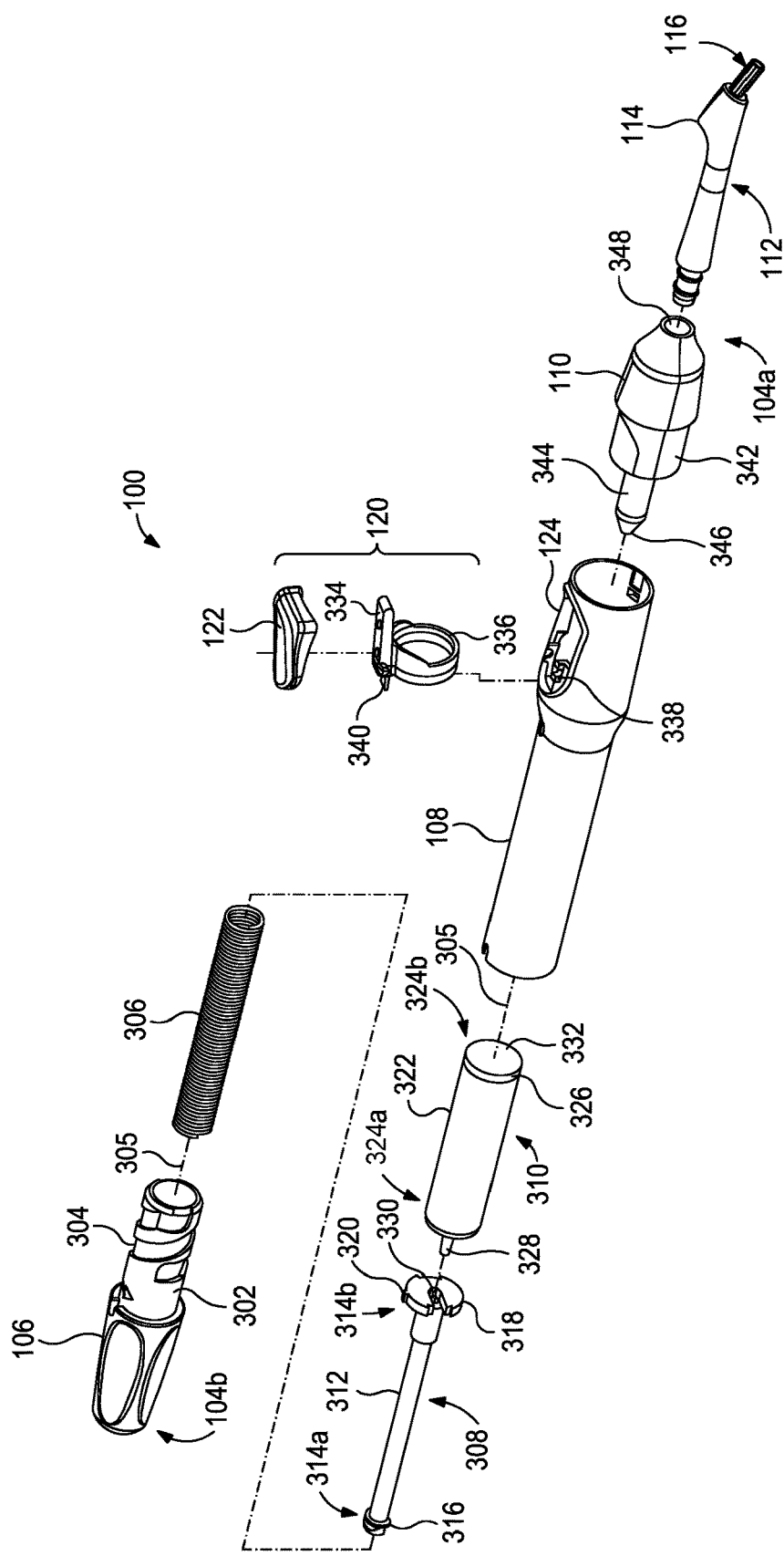
FIG. 3 is an exploded view of the dental solution dispenser of FIG. 1.

FIG. 3 is an exploded view of the dispenser 100, according to one or more embodiments. As illustrated, the twist back 106 includes an axial extension 302 configured to be received within the interior of the grip 108. The axial extension 302 defines a helical slot 304 configured to mate with one or more lugs (not shown) defined or otherwise provided (e.g., molded) on the inner radial surface of the grip 108. Engagement between the lug(s) and the helical slot 304 operates similar to a cam and cam follower mechanism, where the helical slot 304 provides the cam and the lug(s) provide the cam follower configured to ride within the cam. With the lug(s) received within the helical slot 304, rotating the twist back 106 with respect to the grip 108 and about a longitudinal axis 305 of the dispenser 100 allows the lug(s) to ride within and slidingly engage the helical slot 304 and thereby progressively draw the twist back 106 into the interior of the grip 108. Drawing the twist back 106 into the interior of the grip 108 effectively moves the dispenser 100 from the loaded configuration to the primed configuration.

The dispenser 100 further comprises various internal components contained within the body 102 (i.e., the twist back 106, the grip 108, and the front housing 110) including a biasing device 306, a plunger 308, and an ampoule assembly 310. In some embodiments, as illustrated, the biasing device 306 may comprise a coil spring, but could alternatively comprise any other type of spring-like device or mechanism that can be positioned at least partially within the twist back 106 to place an axial load on the plunger 308.

The plunger 308 may comprise an elongate rod 312 that provides a first plunger end 314a and a second plunger end 314b opposite the first plunger end 314a. The first plunger end 314a may be threaded and otherwise define threads 316 configured to be threaded into a corresponding threaded aperture or receptacle (not shown) provided within the interior of the twist back 106. A flange 318 may be provided at the second plunger end 314b and may extend radially outward from the rod 312. In some embodiments, a projection 320 (alternately referred to as a "flag") extends radially from the flange 318 and, as described below, may be configured to be received by and translate within an axial channel defined on the inner radial surface of the grip 108.

The ampoule assembly 310 may include a casing 322 that provides a first ampoule end 324a and a second ampoule end 324b opposite the first ampoule end 324a. The casing 322 may be made of a rigid material, such as a metal (e.g., aluminum), a plastic, or a composite material. The casing 322 may be sized to receive and surround an ampoule 326

(partially shown), which may be filled with a dental solution. The ampoule 326 may also be made of a rigid material, such as a metal, a plastic, or a composite material. In at least one embodiment, the ampoule 326 may be made of a plastic, such as high-density polyethylene. Moreover, in some embodiments, the casing 322 may be omitted from the dispenser 100.

A stud 328 may extend axially from the first ampoule end 324a. The stud 328 may comprise an axial extension of the ampoule 326 and may extend through an aperture (not shown) defined through the first ampoule end 324a of the casing 322. The stud 328 may be configured to be received by a stud aperture 330 defined on the flange 318 at the second plunger end 314b of the plunger 308. The stud 328 may be secured within the stud aperture 330 such that axial movement (or non-movement) of the plunger 308 correspondingly moves (or holds stationary) the ampoule assembly 310 within the body 102 (FIG. 1). This may prove advantageous in protecting and preventing the ampoule 326 from being penetrated prematurely. The stud 328 may be secured within the stud aperture 330 via a variety of means including, but not limited to, a press fit, a bond (e.g., an adhesive), sonic welding, one or more mechanical fasteners (e.g., threading, a snap fit, radial pins, hexagonal coupling, etc.), a collet interface, or any combination thereof.

The ampoule assembly 310 may further include a frangible seal 332 secured to the end of the ampoule 326 to seal the dental solution within the ampoule 326. The frangible seal 332 may be made of a variety of frangible materials including, but not limited to, a metal (e.g., aluminum, copper, tin, etc.), a plastic, paper, and any combination thereof. The frangible seal 332 may be heat sealed to the end of the ampoule 326, but may alternatively be coupled thereto using an adhesive or the like. The frangible seal 332 may provide rigidity, a heat sealable interface, and an impermeable seal until penetrated, as discussed below. In at least one embodiment, the frangible seal 332 may comprise a three-layer bonded film construction consisting of a metal foil interposing a paper backing and a polymer layer, where the polymer layer is sealed to the end of the ampoule 326.

The trigger 120 may include a trigger seat 334 and a catch 336 coupled to or otherwise forming part of the trigger seat 334. The trigger cap 122, as illustrated, may comprise a separate component part that can be secured to the trigger seat 334, such as by a snap fit, or may alternatively form an integral part of the trigger seat 334. In some embodiments, as illustrated, the catch 336 may comprise an annular body sized to receive the ampoule assembly 310 during operation.

More specifically, when the dispenser 100 is assembled, the trigger 120 is received into the grip 108 via the aperture 124 and the catch 336 is configured to receive and engage the ampoule assembly 310 and, more particularly, the outer radial surface of the casing 322. The trigger 120 is able to pivot about a pivot point 338 defined on the grip 108 between the engaged and disengaged positions. In the engaged position, the ampoule assembly 310 is received within the annular body of the catch 336, which engages the outer radial surface of the casing 322 and forms an interference or friction grip that prevents the ampoule assembly 310 from advancing toward the first end 104a of the dispenser 100. In the disengaged position, the trigger 120 pivots to release the catch 336 from the outer radial surface of the casing 322, which allows the ampoule assembly 310 to translate within the body 102 (i.e., the twist back 106, the grip 108, and the front housing 110). As indicated above, a user may be able to transition the trigger 120 between the engaged and disengaged positions by pressing down on the trigger cap 122.

In at least one embodiment, the trigger 120 may include a trigger spring 340 that naturally urges the trigger 120 to the engaged position such that when left unattended, the dispenser 100 naturally prevents discharge of the dental solution. In the illustrated embodiment, the trigger spring 340 comprises an axial extension of the trigger seat 334 configured to engage an inner radial surface of the grip 108 when the trigger 120 is installed. In other embodiments, however, the trigger spring 340 may alternatively comprise any type of biasing device, such as a compression spring or the like. In the illustrated embodiment, pressing down on the trigger cap 122 pivots the catch 336 about the pivot point 338 and thereby flexes the trigger spring 340 (i.e., the axial extension), which builds spring force. Upon removing downward pressure on the trigger cap 122, the spring force urges the trigger 120 to pivot about the pivot point 338 and back to the engaged position.

The front housing 110 provides an axial extension 342 sized and otherwise configured to be received within the interior of the grip 108. The axial extension 342 may facilitate coupling of the front housing 110 to the grip 108. A mandrel 344 extends longitudinally within the front housing 110, including within the axial extension 342. In some embodiments, the mandrel 344 may be coupled to the front housing 110, but the mandrel 344 may alternatively form an integral extension of the front housing 110. A piercing member 346 is provided at the end of the mandrel 344 to be positioned adjacent the frangible seal 332 when the dispenser 100 is fully assembled. A central conduit 348 extends through the mandrel 344 and fluidly communicates with a delivery conduit (not shown) defined through the applicator tip 112. The central conduit 348 may be configured to place the ampoule 326 in fluid communication with the applicator tip 112 via the delivery conduit. As described in more detail below, the piercing member 346 may be configured to pierce and otherwise rupture the frangible seal 332 in order to access and express the dental solution into the central conduit 348, which allows the dental solution to be conveyed to the applicator tip 112 to be discharged via the brush applicator 116.

Figure 4:
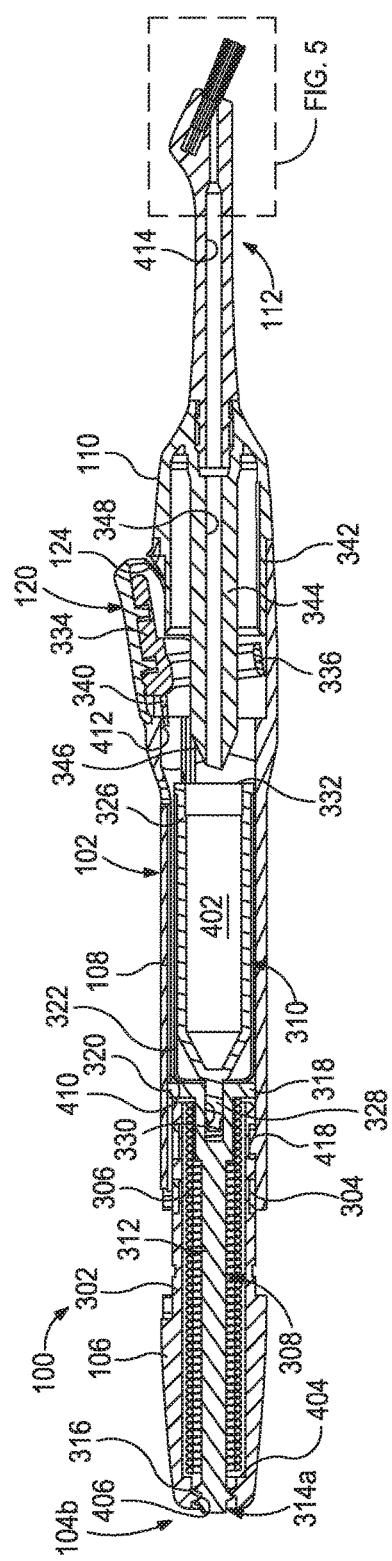
FIG. 4 is a cross-sectional side view of the dental solution dispenser of FIG. 1 as assembled and in the loaded configuration.

FIG. 4 is a cross-sectional side view of the dispenser 100 as assembled and in the loaded configuration, according to one or more embodiments. A fluid chamber 402 is defined within the ampoule 326 to house and otherwise store the dental solution to be discharged (expressed) from the dispenser 100, and the frangible seal 332 seals the dental solution within the fluid chamber 402 until penetrated by the piercing member 346.

In assembling the dispenser 100, the biasing device 306 (e.g., a compression or coil spring) may be extended over the plunger 308 such that the rod 312 extends through the coils of the biasing device 306. The plunger 308 and the biasing device 306 may then be extended within the twist back 106 such that the biasing device 306 interposes the flange 318 and an end wall 404 defined within the interior of the twist back 106. The biasing device 306 may then be axially compressed and the threads 316 defined on the first plunger end 314a may be threaded to the twist back 106 at the second end 104b of the body 102. In at least one embodiment, as indicated above, the threads 316 may be threaded into a threaded aperture or receptacle 406 provided by the twist back 106. Threading the plunger 308 to the threaded receptacle 406 secures the plunger 308 and the biasing device 306 within the twist back 106. Upon activating the dispenser 100, as described below, the plunger 308 may be unthreaded from the twist back 106, thereby allowing the biasing device 306 to expand and urge the plunger 308 toward the applicator tip 112.

The ampoule assembly 310 may then be coupled to the plunger 308 such that the two components remain in a fixed positional relationship through all operational positions during use. The ampoule assembly 310 may be coupled to the plunger 308, for example, by securing the stud 328 within the stud aperture 330 defined on the flange 318, such as via a press fit, a threaded engagement, an adhesive, a sonic weld, one or more mechanical fasteners, or any combination thereof. In the illustrated embodiment, the stud 328 forms an axial extension of the ampoule 326 and extends longitudinally through a hole (not labeled) defined in the casing 322. In other embodiments, however, the stud 328 may alternatively form an axial extension of the casing 322.

The ampoule assembly 310 and the plunger 308 may then be extended axially at least partially into the interior of the grip 108 and the twist back 106 may be secured to the grip 108 for operation. More particularly, the axial extension 302 of the twist back 106 may be received within the interior of the grip 108 until one or more lugs 408 (one shown) defined or otherwise provided on the inner radial surface of the grip 108 mates with the helical slot 304 of the axial extension 302. Moreover, as the axial extension 302 is received within the interior of the grip 108, the projection 320 provided on the flange 318 may be simultaneously received within an axial channel 410 defined on the inner radial surface of the grip 108.

The trigger 120 may be extended through the aperture 124 defined in the grip 108 until the trigger seat 334 is received by the grip 108 at the pivot point 338 (FIG. 3) and the trigger spring 340 is positioned to engage an inner radial surface 412 of the grip 108. The front housing 110 may then be coupled to the grip 108 by extending the axial extension 342 into the interior of the grip 108 and simultaneously extending the mandrel 344 through the annular body of the catch 336. The applicator tip 112 may then be coupled to the front housing 110 to facilitate fluid communication between the central conduit 348 and a delivery conduit 414 defined within the applicator tip 112. The delivery conduit 414 is placed in fluid communication with the central conduit 348 of the mandrel 344 when the applicator tip 112 is coupled to the front housing 110.

Figure 5:
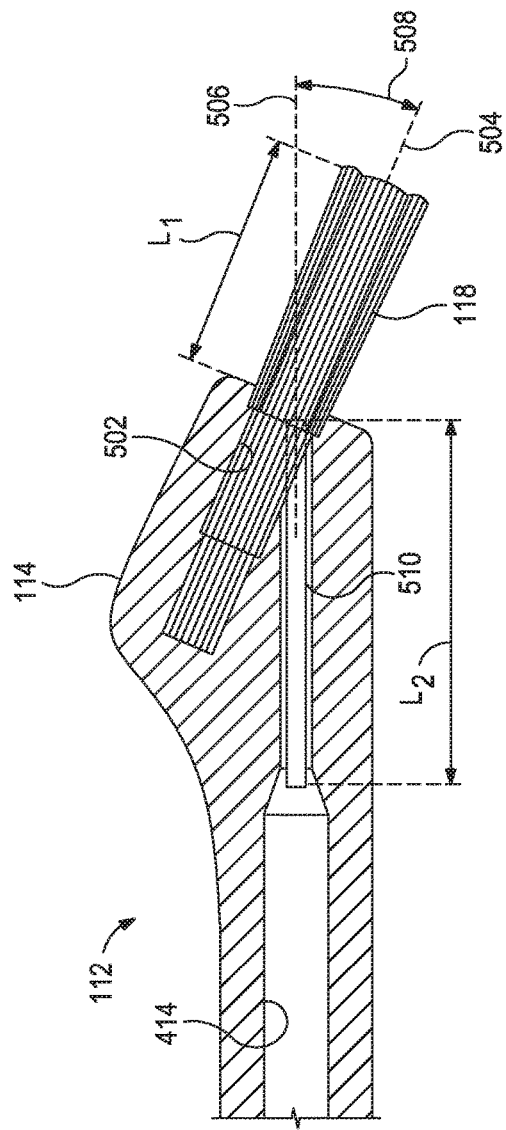
FIG. 5 is an enlarged cross-sectional view of the applicator tip of the dental solution dispenser as indicated by the dashed box in FIG. 4.

FIG. 5 is an enlarged cross-sectional view of the applicator tip 112 indicated by the dashed box in FIG. 4. As illustrated, a brush barrel 502 is defined within the brush cup 114 and the bristles 118 may be disposed within the brush barrel 502 and such that a portion of the bristles 118 extends out of the brush barrel 502 to a predetermined distance or length $L_1$. The actual selected length $L_1$ that the bristles 118 are to extend out of the brush barrel 502 may depend on the viscosity, surface tension, cohesiveness, and other physical properties of the dental solution to be delivered through the applicator tip 112. In at least one embodiment, the length $L_1$ may range between about 0.125 inches and about 0.75 inches. As will be appreciated, however, other ranges for the length $L_1$ that are less than 0.125 inches and greater than 0.75 inches are also contemplated herein, without departing from the scope of the disclosure.

The delivery conduit 414 extends within the applicator tip 112 to the brush cup 114 and thereby places the central conduit 348 (FIGS. 3 and 4) in fluid communication with the brush barrel 502, which may be angularly offset from the delivery conduit 414. More particularly, the brush barrel 502 may have a central axis 504 that is angularly offset from a central axis 506 of the delivery conduit 414 by a predetermined angle 508. The angle 508 of offset between the brush barrel 502 and the delivery conduit 414 may range between about 15° to about 45°. In at least one embodiment, the angle 508 of offset between the brush barrel 502 and the delivery conduit 414 may be about 22.5°.

The angled configuration between the brush barrel 502 and the delivery conduit 414 may prove advantageous in allowing the dental solution to more easily enter the brush applicator 116. More particularly, it can be difficult to express fluids (i.e., the dental solution) through tightly packed bristles 118, which might be present at the bottom of the brush barrel 502. Having the brush barrel 502 extend at the angle 508 allows the delivery conduit 414 to deliver and inject the dental solution to the brush cup 114 at an intermediate location between the bottom of the brush barrel 502 and the exposed ends of the bristles 118. The bristles 118 are less dense at the intermediate location, and thereby more amenable to the introduction of the fluid therethrough.

In some embodiments, a delivery cannula 510 may be positioned within the delivery conduit 414, such as at a reduced diameter section, for example. The delivery cannula 510 may be secured within the delivery conduit 414 using an interference fit between the outer radial surface of the delivery cannula 510 and the inner wall of the delivery conduit 414. In other embodiments, the delivery cannula 510 may be secured within the delivery conduit 414 using an adhesive or an epoxy, or through sonic welding. In any event, the delivery cannula 510 may be secured within the delivery conduit 414 such that it is able to withstand the hydraulic pressures involved in conveying the dental solution through the delivery conduit 414 and into the brush barrel 502.

The delivery cannula 510 may be made of any rigid material including, but not limited to, plastics, metals, ceramics, composite materials, or any combination thereof. The diameter or size of the delivery cannula 510 may vary, depending primarily on the configuration of the dispenser 100 (e.g., the size of the delivery conduit 414) and the type of dental solution being applied with the brush applicator 116. For instance, a larger size cannula may be preferred and employed in order to convey higher viscosity dental solutions. A larger cannula may also allow a dental solution to be applied at an increased flow rate. The delivery cannula 510 may be designed and otherwise manufactured to meet any desired size and application constraints. Exemplary sizes for the delivery cannula 510 may range from about 15 gauge to about 25 gauge. In at least one embodiment, the size of the delivery cannula 510 may range between about 18 gauge to about 20 gauge.

The delivery cannula 510 may exhibit a length $L_2$ that is sufficient to extend at least partially into (i.e., penetrate, enter, etc.) the bristles 118 at an intermediate location between the bottom of the brush barrel 502 and the exposed ends of the bristles 118. Having an end of the delivery cannula 510 at least partially extended into the bristles 118 at the intermediate location may prove advantageous in more efficiently delivering and otherwise expressing the dental solution into portions of the bristles 118 that are less dense. The length $L_2$ may be limited, however, in order to ensure that the delivery cannula 510 does not extend to a point where it may inadvertently contact and damage the teeth of a patient and otherwise obstruct the dental solution application on the teeth.

Figure 6:
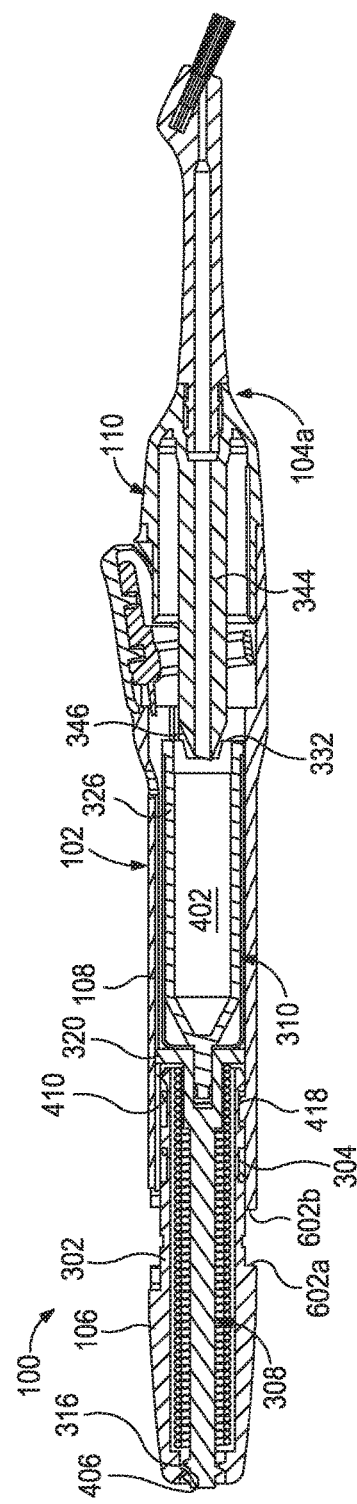
FIGS. 6-10 depict progressive cross-sectional side views of the dental solution dispenser of FIG. 1 during exemplary operation.
Figure 7:
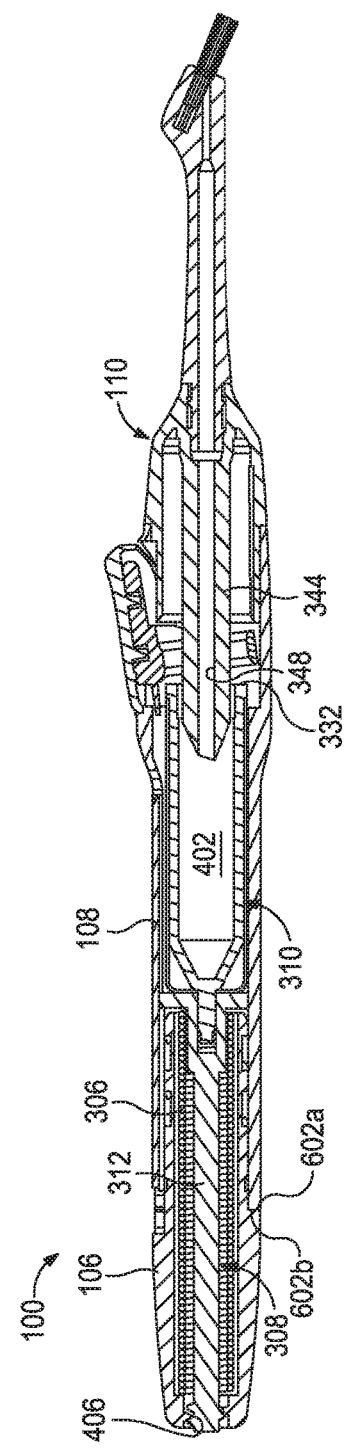
Figure 8:
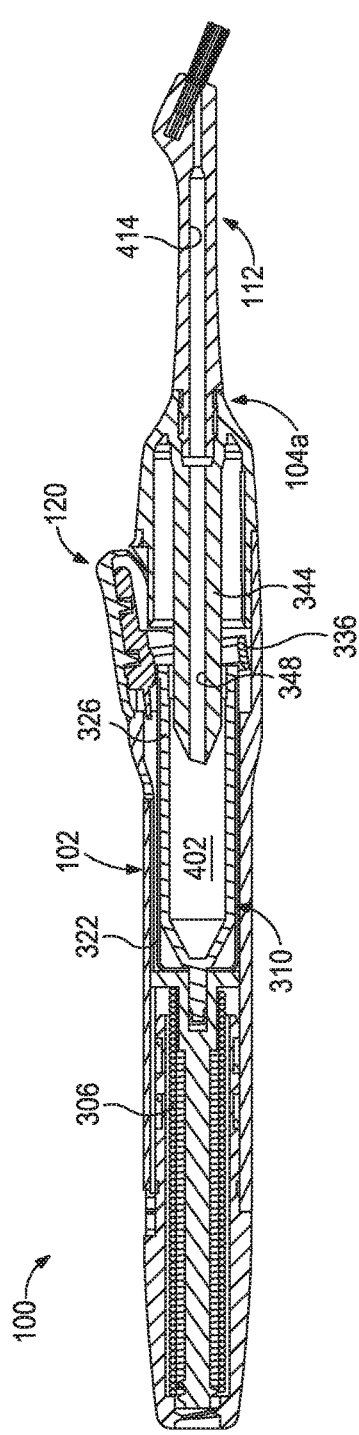
Figure 9:
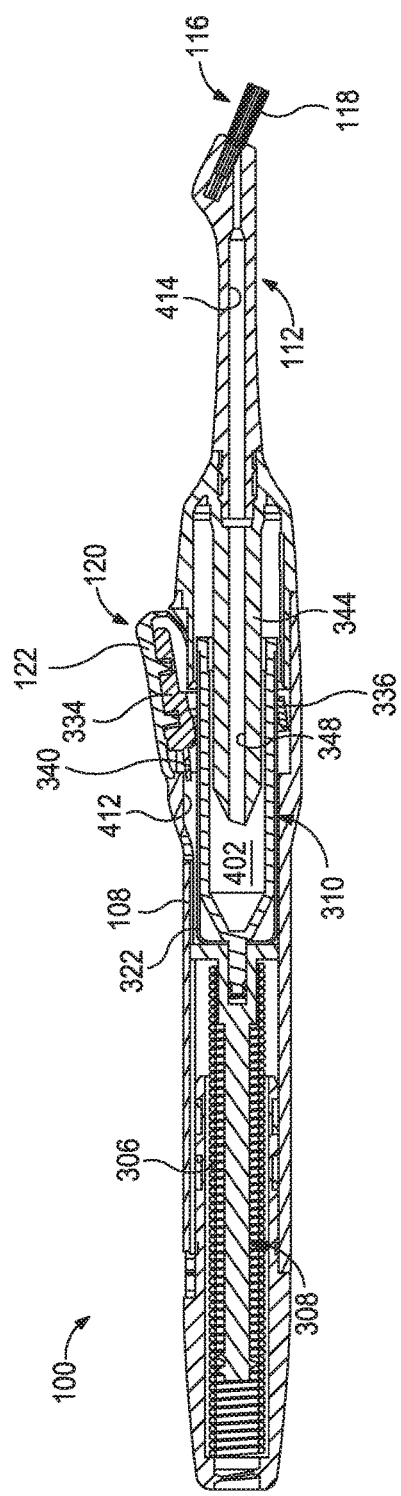
Figure 10:
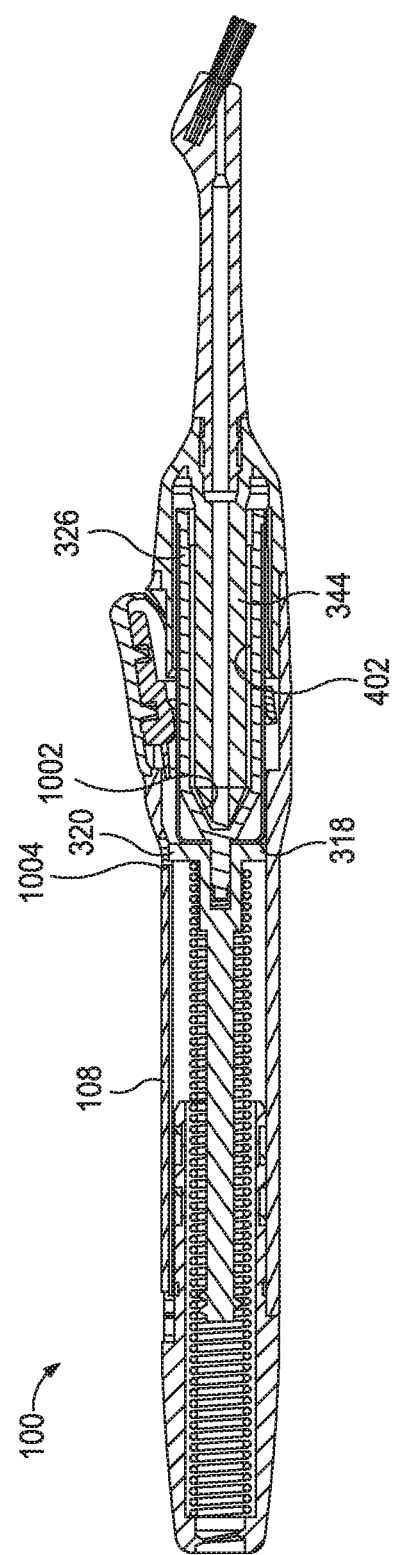

Exemplary operation of the dispenser 100 will now be provided with reference to FIGS. 6-10. FIGS. 6-8 show the dispenser 100 moving to the primed configuration, FIG. 9 shows the dispenser 100 discharging a dental solution from the dispenser 100, and FIG. 10 shows the dispenser 100 in a fully dispensed position.

Referring first to FIG. 6, to move the dispenser 100 from the loaded configuration, as shown in FIG. 4, to the primed configuration, as shown in FIG. 8, a user may grip and angularly rotate the twist back 106 relative to the grip 108. Rotating the twist back 106 relative to the grip 108 allows the lug(s) 418 to slidingly translate within the helical slot 304 and thereby progressively draw the twist back 106, the plunger 308, and the ampoule assembly 310 into the interior of the grip 108 and toward the first end 104a of the body 102. As mentioned above, the helical slot 304 may operate similar to a cam and the lug(s) 418 may operate similar to a cam follower that rides within the helical slot 304.

As the plunger 308 moves axially into the grip 108, the projection 320 simultaneously rides within and slidingly engages the axial channel 410, which prevents the plunger 308 from correspondingly rotating relative to the grip 108 and thereby maintains the plunger 308 in its angular orientation. Maintaining the plunger 308 in its angular orientation as the twist back 106 rotates may allow the plunger 308 to detach from the twist back 106 as the threads 316 gradually unthread from the threaded receptacle 406.

Moreover, as the plunger 308 moves axially into the grip 108, the ampoule 326 is correspondingly moved toward the mandrel 344 until the piercing member 346 penetrates and otherwise pierces the frangible seal 332 to expose the fluid chamber 402. In at least one embodiment, the helical slot 304 does not form a pure helix that exhibits a uniform angular profile (e.g., pitch, lead, etc.) about the axial extension 302 along its axial length. Rather, in some embodiments, the angular profile of the helical slot 304 may be variable and designed and otherwise configured to be less aggressive (e.g., less steep, smaller lead) at the point when the frangible seal 332 is to be pierced by the mandrel 344. In such embodiments, the angular profile of the helical slot 304 may be designed and otherwise configured to become more aggressive (e.g., more steep, larger lead) as the mandrel 344 is forced into the fluid chamber 402.

In FIG. 6, the piercing member 346 is shown penetrating the frangible seal 332, which flares radially outward as the mandrel 344 begins to enter the fluid chamber 402. The mandrel 344 may be sized to fit within the fluid chamber 402, and the fluid chamber 402 may otherwise be sized to receive the mandrel 344. Continued rotation of the twist back 106 with respect to the grip 108 correspondingly urges the ampoule assembly 310 towards the front housing 110, which allows the mandrel 344 to extend deeper into the fluid chamber 402. The twist back 106 may be angularly rotated relative to the grip 108 until an up stop 602a provided on the twist back 106 axially engages a corresponding down stop 602b provided on the grip 108. Axial engagement between the up and down stops 602a,b ceases the axial advancement of the twist back 106, the plunger 308, and the ampoule assembly 310 into and with respect to the grip 108.

FIG. 7 shows the mandrel 344 extending further into the fluid chamber 402 as the twist back 106 is angularly rotated relative to the grip 108. As the mandrel 344 enters the fluid chamber 402, the dental solution stored within the fluid chamber 402 will be forced into the central conduit 348. The mandrel 344 and the fluid chamber 402 may be sized such that a hydraulic seal at the radial interface between the outer radial surface of the mandrel 344 and the inner radial surface of the fluid chamber 402 is generated. Moreover, forcing the frangible seal 332 radially outward with the mandrel 344 may also help form a fluid seal at the radial interface between the mandrel 344 and the fluid chamber 402. As a result, the dental solution may be substantially prevented from migrating out of the fluid chamber 402 via the interface between the mandrel 344 and the fluid chamber 402 and is instead hydraulically forced into the central conduit 348 as the mandrel 344 translates within the fluid chamber 402.

In FIG. 7, the twist back 106 is shown fully rotated with respect to the grip 108 until the up stop 602a of the twist back 106 axially engages the down stop 602b of the grip 108 and thereby ceases the axial advancement of the mandrel 344 into the fluid chamber 402 under user-enabled force. The dispenser 100 may be designed such that as the up stop 602a axially engages the down stop 602b, or at a moment just before such axial engagement, the plunger 308 may be separated from the twist back 106. More particularly, at or just before the moment the up stop 602a axially engages the down stop 602b, the rod 312 may become unthreaded from the threaded receptacle 406, and thereby allowing the biasing device 306 to expand and urge the plunger 308 and the ampoule assembly 310 toward the front housing 110 and the mandrel 344.

In FIG. 8, the catch 336 of the trigger 120 is shown receiving the ampoule assembly 310. More particularly, the trigger 120 is shown in the engaged position, where the catch 336 engages the ampoule assembly 310 (e.g., the casing 322) and thereby stops the axial progression of the ampoule assembly 310 toward the first end 104a of the body 102. As mentioned above, the annular body of the catch 336 may be sized and otherwise configured to receive and engage of the ampoule assembly 310 when the trigger 120 is in the engaged position. In some embodiments, the catch 336 may initially form an interference fit against the outer radial surface of the casing 322 when the trigger 120 is in the engaged position, whereby friction generated at the interface between the ampoule assembly 310 and the catch 336 prevents the ampoule assembly 310 from advancing further. In other embodiments, the catch 336 may be positioned to initially engage the axial end and/or radial extent of the ampoule 326. In such embodiments, once the user first presses the trigger 120, the ampoule assembly 310 may then enter the annular body of the catch 336, after which axial translation of the motion of the ampoule assembly 310 will be governed by friction engagement between the catch 336 and the outer radial surface of the casing 322.

FIG. 8 shows the dispenser 100 in the primed configuration where a small amount of the dental solution stored in the fluid chamber 402 may be expressed (flowed) into the central conduit 348 and subsequently into the applicator tip 112 via the delivery conduit 414. With the ampoule 326 penetrated by the mandrel 344, the dispenser 100 is then "primed" and otherwise ready to dispense the dental solution as desired. At this point, the trigger 120 is in the engaged position such that the ampoule assembly 310 is unable to move any further without pivoting the trigger 120 to the disengaged position, whereupon the catch 336 disengages from the ampoule assembly 310 and allows the biasing device 306 to expand.

In FIG. 9, the ampoule assembly 310 is shown as having advanced further within the grip 108 such that the mandrel 344 has correspondingly advanced further within the fluid chamber 402. Such axial advancement may be facilitated by pressing down on the trigger 120, which releases the catch 336 from engagement with the ampoule assembly 310 (e.g., the casing 322). Once the catch 336 is released, the biasing device 306 is allowed to expand and urge the plunger 308 and the ampoule assembly 310 toward the applicator tip 112, which correspondingly forces the mandrel 344 deeper into the fluid chamber 402. The spring force exhibited by the biasing device 306 may be sufficient to push the ampoule assembly 310 such that the mandrel 344 is extended longitudinally into the fluid chamber 402. Forcing the mandrel 344 into the fluid chamber 402 may generate a fluid dampening effect that prevents the mandrel 344 from extending into the fluid chamber 402 at a high velocity.

As the mandrel 344 moves deeper into the fluid chamber 402, an increasing amount of the dental solution is progressively expressed into the central conduit 348 and conveyed to the brush applicator 116 via the fluidly coupled central conduit 348 and delivery conduit 414. Once in the brush applicator 116, the dental solution may be expressed into the bristles 118 and then flow toward the distal end of the bristles 118 where a user (e.g., a dental practitioner) may apply the dental solution to a desired surface (e.g., a patient's teeth). Releasing the trigger 120 allows the trigger 120 to move back into the engaged position, which stops the axial movement of the ampoule assembly 310 and thereby stops discharge of the dental solution. More particularly, releasing the trigger 120 allows the trigger spring 340 engaged against the inner radial surface 412 of the grip 108 to pivot the trigger seat 334 and the catch 336 back to the engaged position, where the catch 336 again binds against the outer radial surface of the casing 322 to stop axial expansion of the biasing device 306. The user may repeatedly move the trigger 120 between the engaged and disengaged positions to selectively express the dental solution as desired by manipulating or otherwise pressing the trigger cap 122.

In FIG. 10, the dispenser 100 has moved to a fully dispensed position where axial progression of the mandrel 344 within the fluid chamber 402 is stopped once the mandrel 344 reaches and engages a bottom 1002 of the fluid chamber 402. In some embodiments, the dispenser 100 may provide the user with a visual identifier or confirmation when the dispenser 100 has successfully moved to the fully dispensed position. In the illustrated embodiment, for example, the grip 108 may define a window 1004 and, when the dispenser 100 has moved to the fully dispensed position, the flange 318 and the projection 320 defined in the flange 318 may be aligned with the window 1004. Once the flange 318 becomes visible through the window 1004, the user may be assured and otherwise informed that the dispenser 100 has successfully moved to the fully dispensed position.

The embodiments described herein can be readily adapted to include features within the ampoule assembly 310 or the applicator tip 112 to produce turbulent flow or otherwise mixing the dental solution within. Moreover, the embodiments described herein can be readily adapted to simultaneously operate two ampoules 326 each storing a different dental solution, and thereby forming the components of a two-part compound where the flow of the two dental solutions are mixed and dispensed together.

FIG. 11 is a cross-sectional side view of another dental solution dispenser 1100 that may be used to dispense a dental solution as part of dental cleaning, preparation, and restorative processes. The dental solution dispenser 1100 (hereafter "the dispenser 1100") may be similar in some respects to the dispenser 100 of FIGS. 1-10 and, therefore, may be best understood with reference thereto, where like numerals correspond to like elements not described again in detail. As illustrated, for example, the dispenser 1100 may include the body 102 comprising the twist back 106, the grip 108, and the front housing 110. The applicator tip 112 may be coupled to the front housing 110, and the ampoule assembly 310 is positioned within the body 102 (i.e., the grip 108) and coupled to the plunger 308 by receiving the stud 328 into the stud aperture 330 defined in the stud 328. Moreover, the dispenser 1100 may include the trigger 120 received into the grip 108 at the aperture 124 and configured to regulate discharge of the dental solution from the dispenser 1100 by engaging and disengaging the ampoule assembly 310 during operation.

Unlike the dispenser 100 of FIGS. 1-10, however, the axial extension 302 of the twist back 106 defines and otherwise provides a helical protrusion 1102 configured to mate with a helical groove 1104 defined on the inner radial surface of the grip 108. In some embodiments, the helical groove 1104 and the helical protrusion 1102 provide a threaded engagement. With the helical protrusion 1102 received within the helical groove 1104, rotating the twist back 106 relative to the grip 108 allows the helical protrusion 1102 to threadably engage the helical groove 1104 and thereby progressively draw the twist back 106 into the interior of the grip 108. Drawing the twist back 106 into the interior of the grip 108 effectively moves the dispenser 1100 from the loaded configuration to the primed configuration.

Moreover, unlike the dispenser 100 of FIGS. 1-10, the flange 318 of the plunger 308 provides at least one groove 1106 configured to receive one or more collet fingers 1108 (one shown) extending axially from the axial extension 302 of the twist back 106. In some embodiments, as illustrated, the groove 1106 may comprise a plurality of independent or discrete depressions defined in the outer radial surface of the flange 318 and angularly spaced from each other. In such embodiments, each discrete depression may be configured to receive a corresponding one or more of the collet fingers 1108. In other embodiments, however, the groove 1106 may be defined about the entire circumference of the flange 318 and thereby form an annular groove or channel.

Engagement between the collet finger(s) 1108 and the groove(s) 1106 secures the plunger 308 to the twist back 106 such that axial movement of the twist back 106 relative to the grip 108 correspondingly moves the plunger 308 and the ampoule assembly 310 as coupled to the plunger 308. As illustrated, the grip 108 may provide a first inner diameter 1110a and a second inner diameter 1110b, where the second inner diameter 1110b exhibits a larger diameter as compared to the first inner diameter 1110a. The collet finger(s) 1108 are maintained in radial engagement with the groove(s) 1106 while positioned axially within the first inner diameter 1110a since the smaller diameter of the first inner diameter 1110a prevents the collet finger(s) 1108 from radially expanding and thereby disengaging from the groove(s) 1106. When moved axially into the second inner diameter 1110b, however, the collet finger(s) 1108 may be able to radially expand out of engagement with the groove(s) 1106, which then allows the plunger 208 and the ampoule assembly 310 to separate from the twist back 106 and move axially relative to the grip 108.

FIGS. 12A and 12B are isometric views of the axial extension 302 of the twist back 106 engaged and disengaged, respectively, with the plunger 308, according to one or more embodiments. FIG. 12A shows the collet fingers 1108 (two shown) extending longitudinally from the axial extension 302 and engaged with the groove(s) 1106. In the illustrated embodiment, each collet finger 1108 is received into a corresponding discrete groove 1106, which allows rotational movement of the twist back 106 to be transferred to the plunger 308 and the ampoule assembly 310 (FIG. 11) as coupled to the plunger 308 at the stud aperture 330. In other embodiments, however, as indicated above, the groove(s) 1106 may be defined about the entire circumference of the flange 318 and thereby form a continuous annular groove or channel. In such embodiments, mutual rotation of the twist back 106 and the plunger 308 may nonetheless be accomplished either through a secure coupling of the stud 328 (FIG. 11) into the stud aperture 330 or by a gripped engagement between the collet fingers 1108 and the groove(s) 1106.

In FIG. 12B, the collet fingers 1108 are shown disengaged from the groove(s) 1106. As illustrated, the collet fingers 1108 may disengage from the groove(s) 1106 as the plunger 208 continues to move axially relative to the twist back 106. Opposing angled surfaces defined on the collet fingers 1108 and the groove(s) 1106 may help urge the collet fingers 1108 radially outward and out of engagement with the groove(s) 1106 as the plunger 208 moves axially relative to the twist back 106.

The helical protrusion 1102 defined on the axial extension 302 is also depicted in FIGS. 12A and 12B. The design of the helical protrusion 1102 (i.e., thread pitch, thread lead, etc.) may vary depending on the application and configuration of the dispenser 1100 (FIG. 11). In at least one embodiment, as illustrated, the helical protrusion 1102 may define a full revolution about the axial extension 302. In other embodiments, however, the helical protrusion 1102 may be defined about the axial extension 302 for less than or more than a full revolution, without departing from the scope of the disclosure.

Referring again to FIG. 11, the dispenser 1100 may be assembled similar to assembly of the dispenser 100 of FIGS. 1-10, as described above. The biasing device 306 is extended over the plunger 308 such that the rod 312 extends through the coils of the biasing device 306, and the plunger 308 and the biasing device 306 are then extended within the twist back 106 such that the biasing device 306 interposes the flange 318 and the end wall 404 of the twist back 106. The biasing device 306 is then axially compressed and the collet fingers 1108 may be received within the groove(s) 1106. In some embodiments, the first plunger end 314a extends at least partially into the receptacle 406 provided by the twist back 106. Upon activating the dispenser 1100, as described below, the collet fingers 1108 become disengaged from the groove(s) 1106, thereby allowing the biasing device 306 to expand and urge the plunger 308 toward the applicator tip 112.

The ampoule assembly 310 is then coupled to the plunger 308 by securing the stud 328 within the stud aperture 330 defined on the flange 318. The ampoule assembly 310 and the plunger 308 are then extended axially at least partially into the interior of the grip 108 and the twist back 106 may be secured to the grip 108 by threading the helical protrusion 1102 into the helical groove 1104 a short distance. The trigger 120 is extended through the aperture 124 defined in the grip 108 until the trigger seat 334 is received by the grip 108 at the pivot point 338 (FIG. 3). The front housing 110 is then coupled to the grip 108 by extending the axial extension 342 into the interior of the grip 108 and simultaneously extending the mandrel 344 through the annular body of the catch 336. The applicator tip 112 is then coupled to the front housing 110, as described above.

Figure 13:
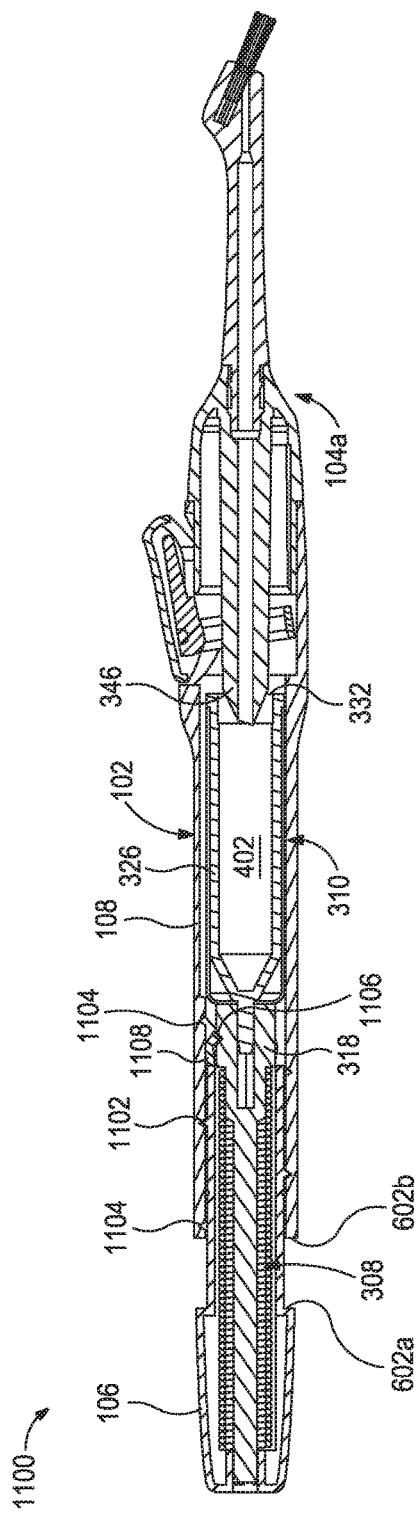
FIGS. 13-16 depict progressive cross-sectional side views of the dental solution dispenser of FIG. 11 during exemplary operation.
Figure 14:
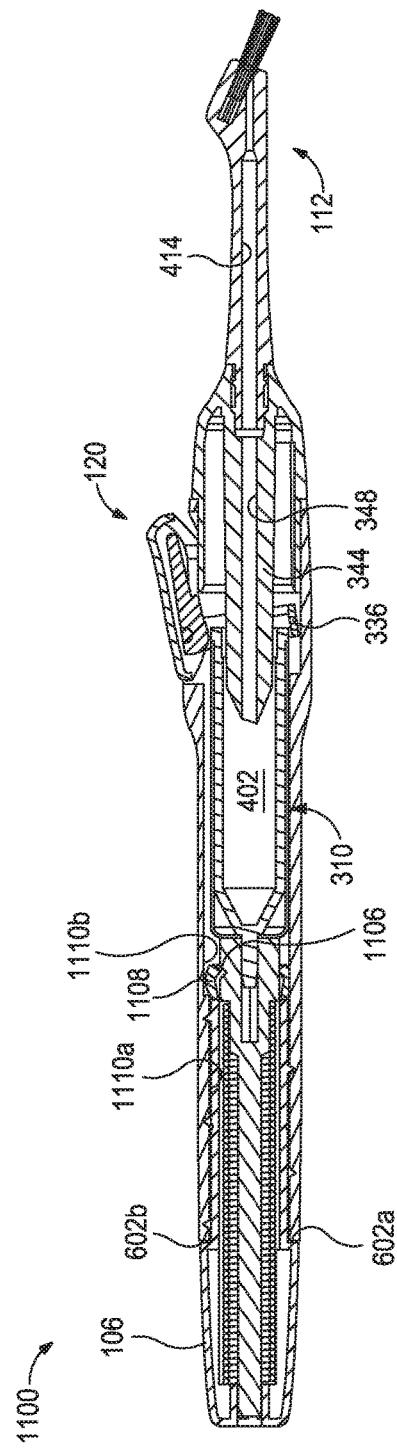
Figure 15:
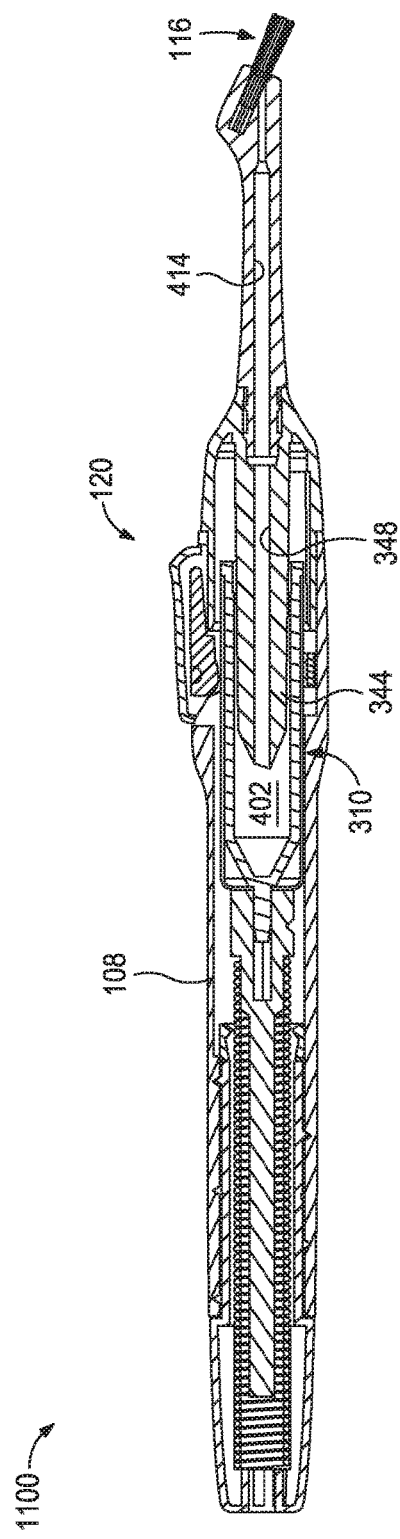
Figure 16:
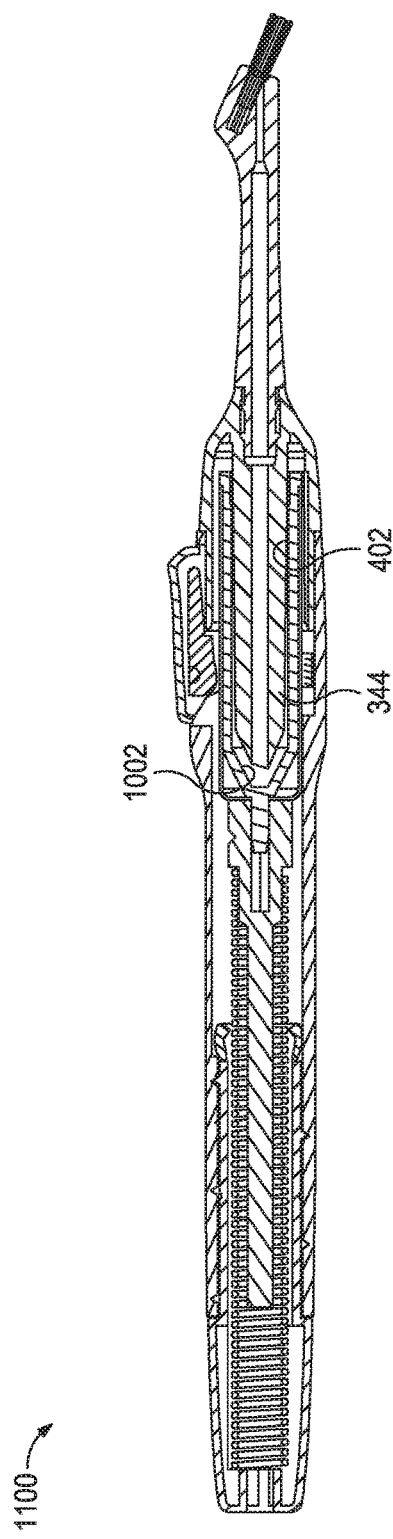

Exemplary operation of the dispenser 1100 will now be provided with reference to FIGS. 13-16. FIGS. 13 and 14 show the dispenser 1100 moving to the primed configuration, FIG. 15 shows the dispenser 1100 in the process of discharging a dental solution from the dispenser 1100, and FIG. 16 shows the dispenser 1100 in a fully dispensed position.

Referring first to FIG. 13, to move the dispenser 1100 from the loaded configuration, as shown in FIG. 11, to the primed configuration, as shown in FIG. 14, a user may grip and angularly rotate the twist back 106 relative to the grip 108. Rotating the twist back 106 relative to the grip 108 allows the helical protrusion 1102 to advance into the helical groove 1104 and thereby progressively draw the twist back 106, the plunger 308, and the ampoule assembly 310 axially into the interior of the grip 108 and toward the first end 104a of the body 102. As the plunger 308 moves axially into the grip 108, the ampoule 326 is correspondingly moved toward the mandrel 344 and the piercing member 346 is able to engage and pierce the frangible seal 332 to expose the fluid chamber 402. In embodiments where the groove 1106 comprises an annular channel, the collet finger(s) 1108 may not provide a sufficient grip on the flange 318 to urge the ampoule 326 to rotate with rotation of the twist back 106. In such embodiments, the frangible seal 332 may be penetrated solely through axial movement of the ampoule 326. Alternatively, in embodiments where each collet finger 1108 is received within a discrete groove 1106, or alternatively where the collet fingers 118 grippingly engage the groove 1106, the ampoule 326 may rotate and axially translate as the piercing member 346 penetrates the frangible seal 332.

As the plunger 308 moves axially into the grip 108, the collet finger(s) 1108 are maintained in radial engagement with the groove(s) 1106 while axially positioned within the first inner diameter 1110a. Continued rotation of the twist back 106 relative to the grip 108 correspondingly urges the ampoule assembly 310 towards the front housing 110, which allows the mandrel 344 to extend deeper into the fluid chamber 402. The twist back 106 may be angularly rotated relative to the grip 108 until the up stop 602a provided on the twist back 106 axially engages a corresponding down stop 602b provided on the grip 108. Axial engagement between the up and down stops 602a,b ceases the axial advancement of the twist back 106, the plunger 308, and the ampoule assembly 310 into and with respect to the grip 108.

FIG. 14 shows the mandrel 344 extending further into the fluid chamber 402 as the twist back 106 is angularly rotated relative to the grip 108. As the mandrel 344 enters the fluid chamber 402, the dental solution stored within the fluid chamber 402 will be forced into the central conduit 348. The twist back 106 is shown fully rotated relative to the grip 108 where the up stop 602a of the twist back 106 axially engages the down stop 602b of the grip 108 and thereby ceases the axial advancement of the mandrel 344 into the fluid chamber 402 under user-enabled force.

In some embodiments, the dispenser 1100 may be designed such that as the up stop 602a axially engages the down stop 602b, or at a moment just before such axial engagement, the collet finger(s) 1108 may be located within the second inner diameter 1110b of the grip, which allows the collet finger(s) 1108 to separate from the groove(s) 1106. More specifically, once the collet finger(s) 1108 enter the second inner diameter 1110b, the collet finger(s) 1108 are no longer radially constrained by the smaller inner diameter of the first inner diameter 1110a. As a result, the collet finger(s) 1108 may be able to radially expand out of engagement with the groove(s) 1106. In the illustrated embodiment, the spring force of the biasing device 306 may urge the plunger 308 and the ampoule assembly 310 toward the front housing 110 relative to the twist back 106, which may force the collet finger(s) 1108 to radially expand out of engagement with the groove(s) 1106.

At this point, the catch 336 of the trigger 120 may be configured to receive the ampoule assembly 310 within its annular body. More particularly, the trigger 120 is shown in the engaged position, where the catch 336 engages the ampoule assembly 310 and thereby stops the axial progression of the ampoule assembly 310 toward the first end 104a of the body 102. With the catch 336 engaging the ampoule assembly 310, the dispenser 1100 will be in the primed configuration and a small amount of the dental solution stored in the fluid chamber 402 may be expressed (flowed) into the central conduit 348 and subsequently into the applicator tip 112 via the delivery conduit 414. The dispenser 1100 is then ready to dispense the dental solution as desired by pivoting the trigger 120 to the disengaged position, whereupon the catch 336 disengages from the ampoule assembly 310 and allows the biasing device 306 to expand.

In FIG. 15, the ampoule assembly 310 is shown as having advanced further within the grip 108 such that the mandrel 344 has correspondingly advanced further within the fluid chamber 402. As described above, such axial advancement may be facilitated by pressing down on the trigger 120 to release the catch 336 and allow the biasing device 306 to expand and urge the plunger 308 and the ampoule assembly 310 toward the applicator tip 112. As the mandrel 344 moves deeper into the fluid chamber 402, the dental solution is progressively expressed into the central conduit 348 and conveyed to the brush applicator 116 via the fluidly coupled central conduit 348 and delivery conduit 414. Releasing the trigger 120 allows the trigger 120 to move back into the engaged position, which stops the axial movement of the ampoule assembly 310 and thereby stops discharge of the dental solution.

In FIG. 16, the dispenser 1100 has moved to a fully dispensed position where axial progression of the mandrel 344 within the fluid chamber 402 is stopped once the mandrel 344 reaches and engages the bottom 1002 of the fluid chamber 402.

Figure 17A:
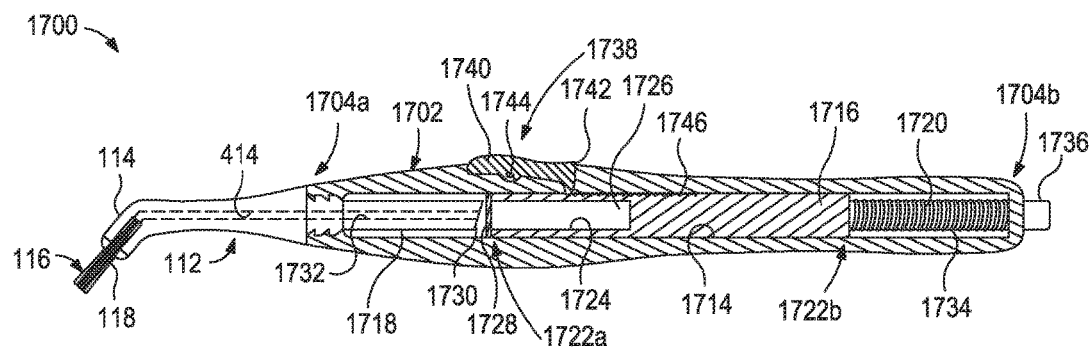
FIGS. 17A and 17B are partial cross-sectional side and exploded isometric views, respectively, of another example dental solution dispenser.
Figure 17B:
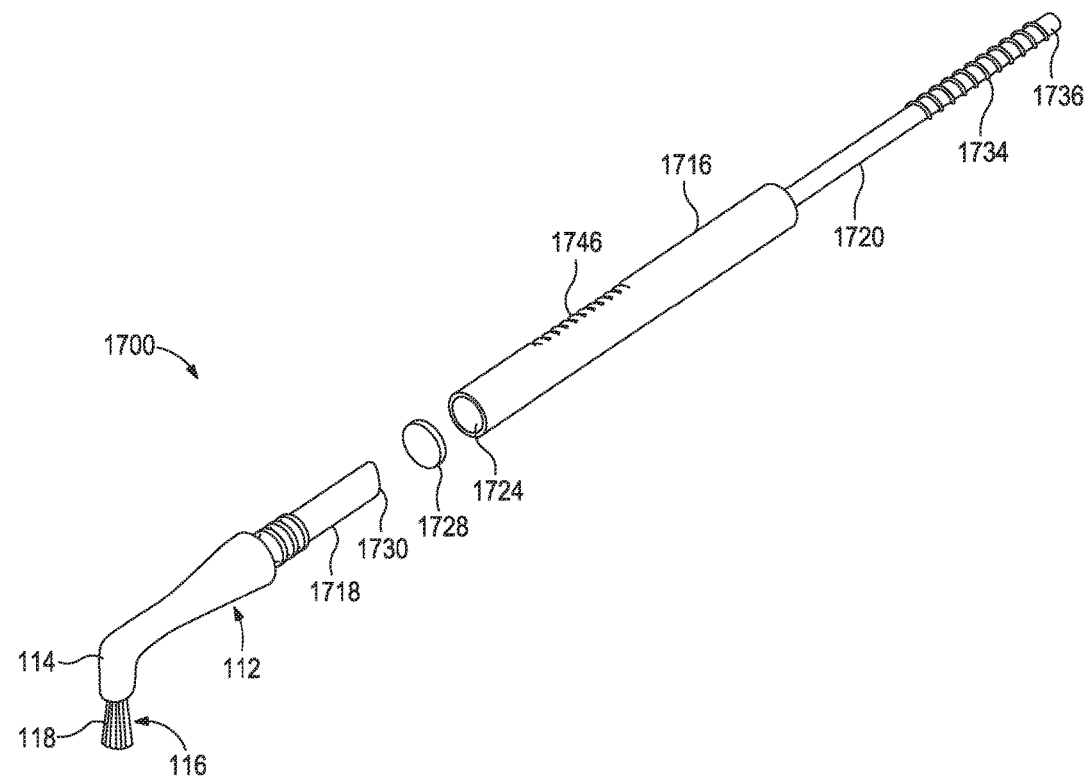

FIGS. 17A and 17B are partial cross-sectional side and exploded isometric views, respectively, of another example dental solution dispenser 1700 that may be used to dispense a dental solution as part of dental cleaning, preparation, and restorative processes, according to one or more embodiments. The dental solution dispenser 1700 (hereafter "the dispenser 1700") may be similar in some respects to the dispensers 100, 1100 of FIGS. 1-10 and FIGS. 11-16, respectively, and therefore may be best understood with reference thereto. As illustrated in FIG. 17A, the dispenser 1700 may include a generally elongate body 1702 having a first end 1704a and a second end 1704b. The body 1702 may be made of similar materials as the body 102 of the dispenser 100 of FIGS. 1-10. The applicator tip 112 may be coupled to the body 1702 at the first end 1704a and, as described above, includes the brush cup 114 that receives the brush applicator 116 made of the bristles 118.

The body 1702 defines and otherwise provides a hollow interior 1714 that extends substantially between the first and second ends 1704a,b. The interior 1714 may be configured to receive and house an ampoule 1716, a mandrel 1718, and a plunger 1720. The ampoule 1716 may be similar in some respects to the ampoule 326 or the ampoule assembly 310 described herein above with respect to the dispensers 100, 1100 of FIGS. 1-10 and FIGS. 11-16, respectively. As illustrated, the ampoule 1716 provides an ampoule first end 1722a and an ampoule second end 1722b opposite the ampoule first end 1722a. The ampoule 1716 may be made of the same materials as the ampoule 326 described above. A fluid chamber 1724 may be defined within the ampoule 1716 at the ampoule first end 1722a and may be configured to house (store) a dental solution 1726. A frangible seal 1728 may be secured to the ampoule first end 1722a to thereby seal the dental solution 1726 within the fluid chamber 1724. The frangible seal 1728 may be the same as or similar to the frangible seal 332 described herein with respect to the dispensers 100, 1100 of FIGS. 1-10 and FIGS. 11-16, respectively, and, therefore, will not be described again in detail.

The mandrel 1718 is arranged within the interior 1714 at the first end 1704a and may extend longitudinally from the applicator tip 112. In some embodiments, the mandrel 1718 may be coupled to the applicator tip 112, but the mandrel 1718 may alternatively form an integral extension of the applicator tip 112. The mandrel 1718 may provide and otherwise define a piercing member 1730 disposed adjacent the frangible seal 1728 when the dispenser 1700 is assembled. A central conduit 1732 may be defined in and otherwise extend through the mandrel 1718 and fluidly communicate with the applicator tip 112 to fluidly communicate with the delivery conduit 414 of the applicator tip 112. As described in more detail below, the piercing member 1730 may be configured to pierce and otherwise rupture the frangible seal 1728 in order to access and express (flow) the dental solution 1726 into the central conduit 1732 to be conveyed to the applicator tip 112. Accordingly, the central conduit 1732 may be configured to place the fluid chamber 1724 in fluid communication with the brush applicator 116 and, more particularly, with the bristles 118.

The plunger 1720 may generally interpose the ampoule 1716 and the second end 1704b of the body 1702. In some embodiments, the plunger 1720 may comprise a separate and individual component coupled to the ampoule 1716 at the ampoule second end 1722b. In other embodiments, however, the plunger 1720 may comprise an integral axial extension of the ampoule 1716 and extend longitudinally from the ampoule second end 1722b.

A biasing device 1734 may be arranged within the interior 1714 and also interposing the ampoule 1716 and the second end 1704b of the body 1702. The biasing device 1734 may comprise a coil spring, but could alternatively comprise any other type of spring-like device or mechanism that can be positioned in the body 1702 to place an axial load on the ampoule 1716. As illustrated, the biasing device 1734 may be positioned about the plunger 1720 such that the plunger 1720 extends through the biasing device 1734. Upon activating the dispenser 1700, the biasing device 1734 is allowed to expand and thereby urge the ampoule 1716 toward the applicator tip 112.

The dispenser 1700 may further include an activation button 1736 disposed at the second end 1704b of the body 1702 and otherwise extending from the second end 1704b on the exterior of the body 1702. In some embodiments, the activation button 1736 may comprise an axial extension of the plunger 1720. Accordingly, in some embodiments, the plunger 1720 and the activation button 1736 may comprise axial extensions of the ampoule 1716 and may otherwise all form a monolithic elongate component of the dispenser 1700. In other embodiments, however, the activation button 1736 may comprise a separate structural component able to act on the plunger 1720.

The dispenser 1700 may further include a trigger 1738 coupled to the body 1702 at an intermediate location between the first and second ends 1704a,b and extending at least partially into the interior 1714. As best seen in FIG. 17A, the trigger 1738 may include a thumb pad 1740 at one end and a catch 1742 at the opposing end. The trigger 1738 may be pivotably coupled to the body 1702 at a pivot point 1744 and may be configured to pivot between an engaged position, where the catch 1742 engages the ampoule 1716, and a disengaged position, where the catch 1742 releases from ampoule 1716. In some embodiments, a plurality of teeth or ridges 1746 may be defined on the outer surface of the ampoule 1716 and the catch 1742 may be configured to engage the ridges 1746 when in the engaged position and disengage (release from) the ridges 1746 upon pivoting back to the disengaged position. A user may be able to move the trigger 1738 between the engaged and disengaged positions by manipulating or otherwise pressing the thumb pad 1740. In at least one embodiment, the trigger 1738 may be spring loaded and thereby exhibit a natural tendency to move to the engaged position. In other embodiments, however, the user may be required to move the trigger 1738 back to the engaged position.

In example operation, a user may activate the dispenser 1700 by pressing (actuating) the activation button 1736, which causes the plunger 1716 to move the ampoule 1716 toward the applicator tip 112 and otherwise into contact with the mandrel 1718. As the ampoule 1716 contacts the mandrel 1718, the piercing member 1730 may penetrate and otherwise pierce the frangible seal 1728 and thereby expose the fluid chamber 1724. At this point, the trigger 1738 may be in the engaged position such that the ampoule 1716 may be unable to move any further without pivoting the trigger 1738 to the disengaged position, whereupon the catch 1742 disengages from the ridges 1746 and thereby allows the biasing device 1734 to expand. The spring force exhibited by the biasing device 1734 may be sufficient to push the ampoule 1716 further toward the applicator tip 112 as it is biased against an end wall within the interior 1714 at or near the second end 1704b of the body 1702.

The mandrel 1718 may be sized to fit within the fluid chamber 1724, and the fluid chamber 1724 may otherwise be sized to receive the mandrel 1718. Accordingly, as the biasing device 1734 urges the ampoule 1716 toward the applicator 100, the mandrel 1718 may be progressively received within the fluid chamber 1724. As the mandrel 1718 enters the fluid chamber 1724, the dental solution 1726 may be forced into the central conduit 1732. The mandrel 1718 and the fluid chamber 1724 may be sized such that a hydraulic seal at the radial interface between the two components is generated. As a result, the dental solution 1726 may be substantially prevented from migrating out of the fluid chamber 1724 via the interface between the mandrel 1718 and the fluid chamber 1724 and is instead hydraulically forced into the central conduit 1732. As indicated above, the central conduit 1732 may deliver and otherwise convey the dental solution 1726 to the brush applicator 116. Once in the brush applicator 116, the dental solution 1726 is expressed into the bristles 118 to be applied to a desired surface, such as the teeth of a patient.

In some embodiments, the user may stop the flow of the dental solution 1726 by moving the trigger 1738 back to the engaged position. This may be done either manually by pivoting the trigger 1738 until the catch 1742 again engages the ridges 1746, or through spring action, as mentioned above. In some embodiments, the user may be required to press the trigger 1738 multiple times while expressing the dental solution 1726 during a dental treatment operation, where each press (actuation) of the trigger 1738 allows the ampoule 1716 to advance a predetermined distance (i.e., to the next ridge 1746), and thereby express a predetermined amount of the dental solution 1726.

Figure 18A:
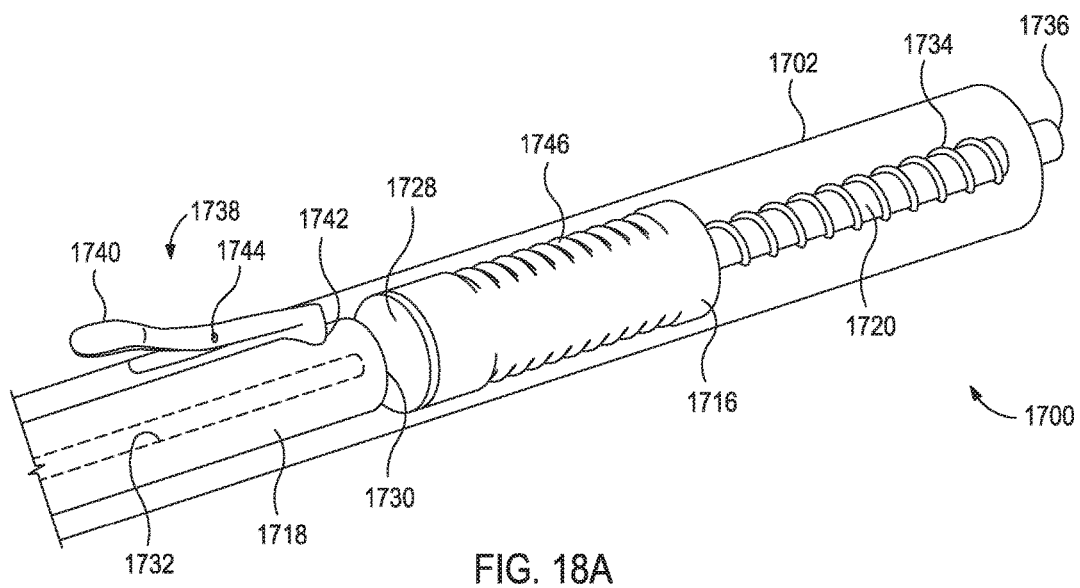
FIGS. 18A-18C depict various configurations of the trigger the dental solution dispenser of FIGS. 17A-17B.
Figure 18B:
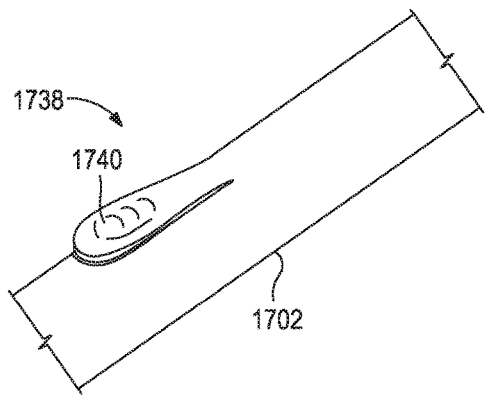
Figure 18C:
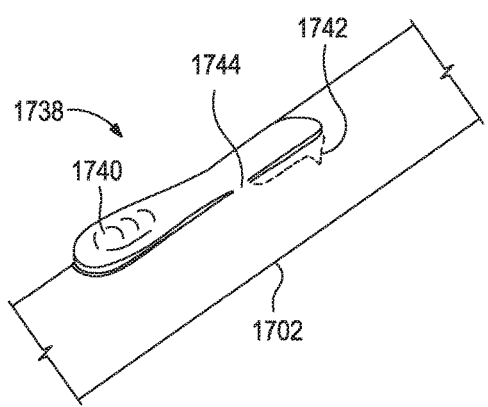

FIGS. 18A-18C depict various configurations of the trigger 1738, according to one or more embodiments. In FIG. 18A, as described above, the trigger 1738 is pivotably coupled to the body 1702 at the pivot point 1744 and includes the thumb pad 1740 at one end and the catch 1742 at the opposing end. In the illustrated embodiment, a user activates the dispenser 1700 by pressing the activation button 1736, which causes the ampoule 1716 to move axially within the body 1702 and into contact with the mandrel 1718. Upon contacting the mandrel 1718, the frangible seal 1728 will be penetrated by the piercing member 1730 and thereby expose the fluid chamber 1728. At this point, forward pressure on the trigger 1738 and, more particularly, on the thumb pad 1740, lifts the catch 1742 out of engagement with the ampoule 1716 as the trigger 1738 pivots about the pivot point 1744. The biasing device 1734 may then be free to urge the ampoule 1716 further toward the applicator tip 112 (FIGS. 17A-17B) and receive the mandrel 1718 within the fluid chamber 1724. As the mandrel 1718 enters the fluid chamber 1724, the dental solution 1726 is forced into the central conduit 1732 and conveyed to the applicator tip 112 for dispensing.

In FIG. 18B, the trigger 1738 is depicted as a thin plastic projection or flap that is naturally biased away from the body 1702. A user may press down on the thumb pad 1740 and thereby generate friction between the underside of the thumb pad 1740 and the outer surface of the ampoule 1716 (FIG. 18A) and thereby slow or stop the axial progress of the ampoule 1716. In such embodiments, the catch 1742 (FIG. 18A) and the ridges 1746 (FIG. 18A) may be omitted but may alternatively be included, without departing from the scope of the disclosure.

In FIG. 18C, the trigger 1738 is again depicted as a thin plastic projection or flap that is naturally biased away from the body 1702, but pivotable about the pivot point 1744, which forms a part of the body 1702. In the illustrated embodiment, the trigger 1738 is naturally biased to the disengaged position and a user may be able to press down on either the front or the back of the trigger 1738 to stop or slow axial movement of the ampoule 1716. Pressing down on the thumb pad 1740, for example, will generate a friction engagement with the outer surface of the ampoule 1716 (FIG. 18A) and thereby slow or stop discharge of the dental solution 1726. Pressing down on the back of the trigger 1738 will force the catch 1742 into engagement with the ridges 1746 (FIG. 18A) to stop or slow axial movement of the ampoule 1716. Accordingly, axial movement of the ampoule 1716 may be stopped or slowed by friction applied against the outer surface of the ampoule 1716 or otherwise reengaging the catch 1742 with the ridges 1746.

In some embodiments, the trigger 1738 may be pressed once and the entirety of the dental solution 1726 may be dispensed or until another action is taken. In other embodiments, the trigger 1738 may be pressed once and the dispenser 1700 may be configured to dispense until the next ridge 1746 is engaged by the catch 1742. In other embodiments, a user may press and hold the trigger 1738 to initiate dispensing and until the fluid chamber 1724 empties or another action is taken. In other embodiments, a user must press and hold the trigger 1738 to halt dispensing. In other embodiment, pressing and holding the trigger 1738 may only slow the rate of dispensing.

Figure 19:
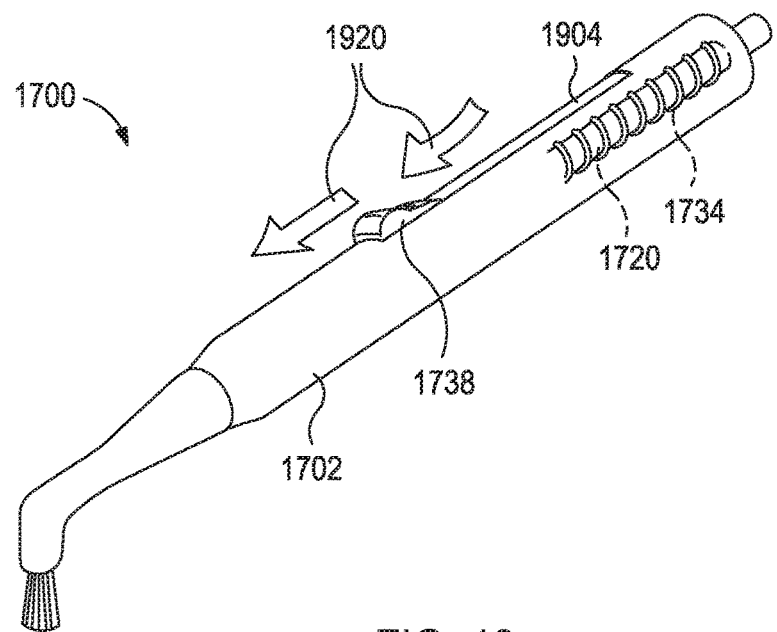
FIG. 19 is an isometric view of another embodiment of the dental solution dispenser of FIGS. 17A-17B.

FIG. 19 is an isometric view of another embodiment of the dispenser 1700, according to one or more embodiments. More particularly, FIG. 19 depicts an alternative means of activating or otherwise manipulating the plunger 1720 to initiate and control operation of the dispenser 1700. The plunger 1720 in FIG. 19 may be operatively coupled to or otherwise replace the trigger 1738. Consequently, actuation of the plunger 1730 may be finger-assisted at the trigger

1738. As illustrated, the plunger 1720 may be moved in the direction indicated by the arrows 1920 along a channel 1904 defined in the body 1702. As will be appreciated, this may allow the user to increase the rate of dispensing by applying forward directional force in the direction of the arrows 1920 and thereby supplement the spring force of the biasing device 1734. This may also allow the user to decrease the rate of dispensing by applying rearward directional force to the plunger 1720 in a direction opposite that of the arrows 1902, and thereby reducing the spring force on the ampoule 1716. Moreover, this may further allow the user to halt dispensing of the dental solution 1726 by applying additional rearward directional force to fully counteract the spring force on the plunger 1720.

Figure 20:
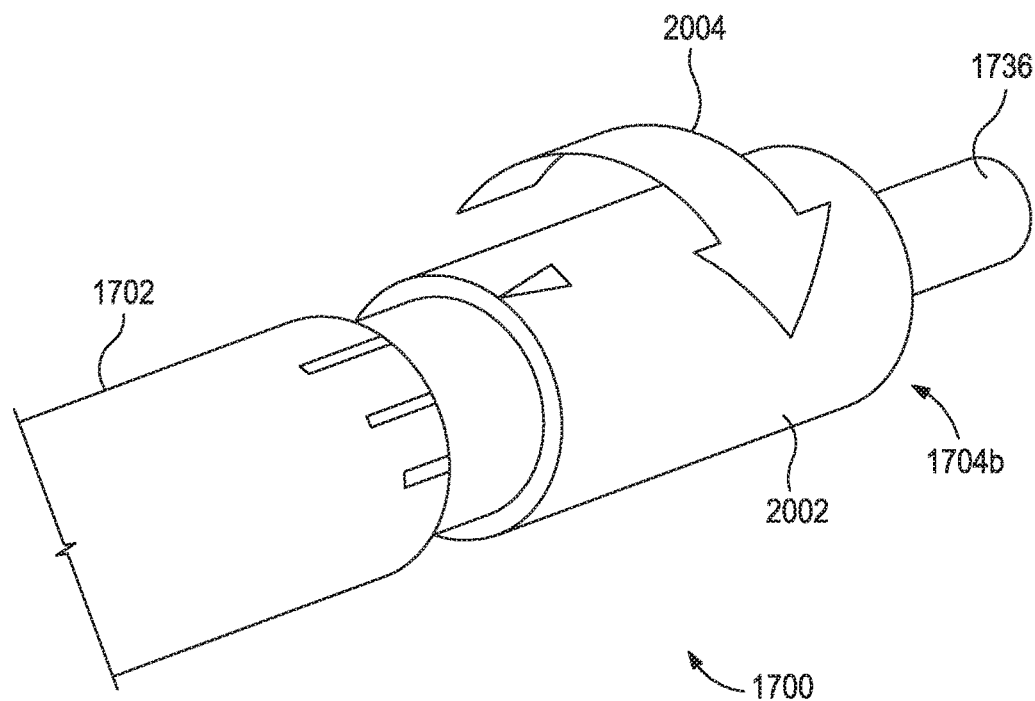
FIG. 20 depicts another embodiment of the dental solution dispenser of FIGS. 17A-17B.

FIG. 20 depicts another way to vary the rate of dispensing the dental solution from the dispenser 1700. As illustrated, an end cap 2002 may be positioned at the second end 1704b of the body 1702 of the dispenser 1700. Rotating end cap 2002 in the direction of the arrow 2004 may cause the end cap 2002 to advance or retreat along internal mating threads (not shown), and thereby increase or decrease compression of the biasing device 1734 (FIGS. 17A-17B). As a result, the force on the ampoule 1716 (FIGS. 17A-17B) may correspondingly be increased or decreased, depending on which way the end cap 2002 is rotated.

Figure 21A:
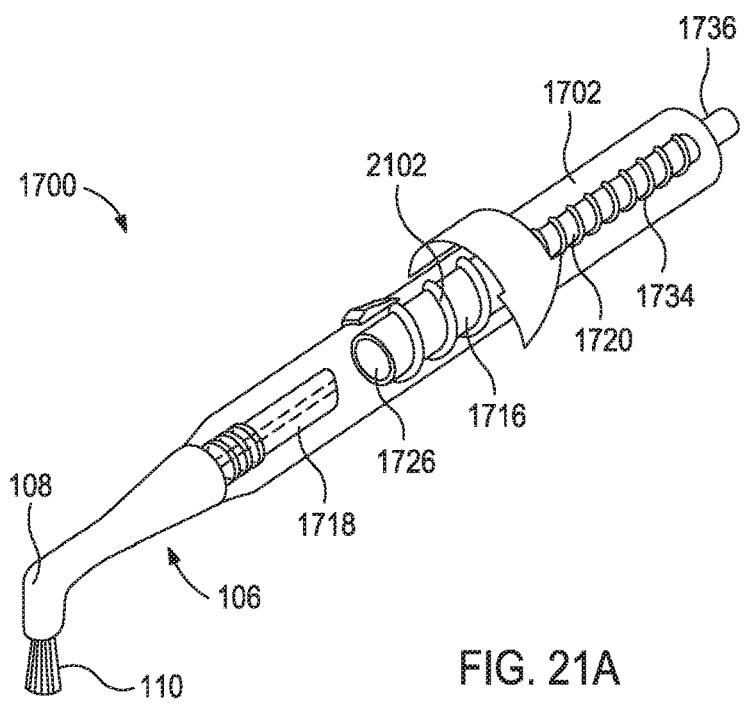
FIGS. 21A-21C illustrate another embodiment of the dental solution dispenser of FIGS. 17A-17B.
Figure 21B:
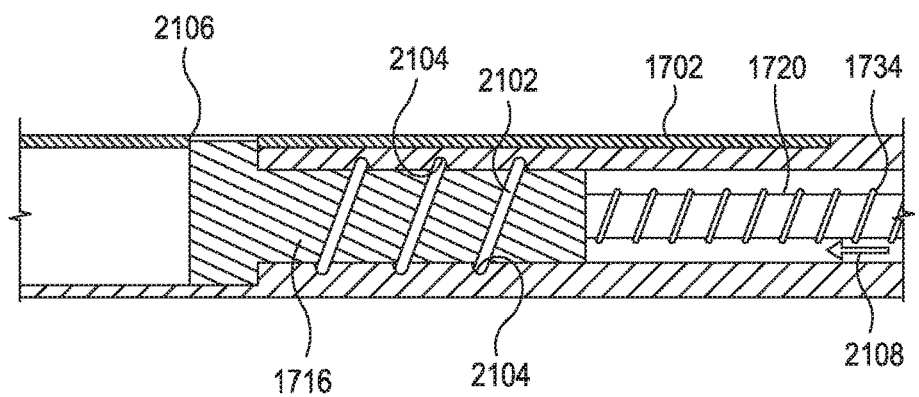
Figure 21C:
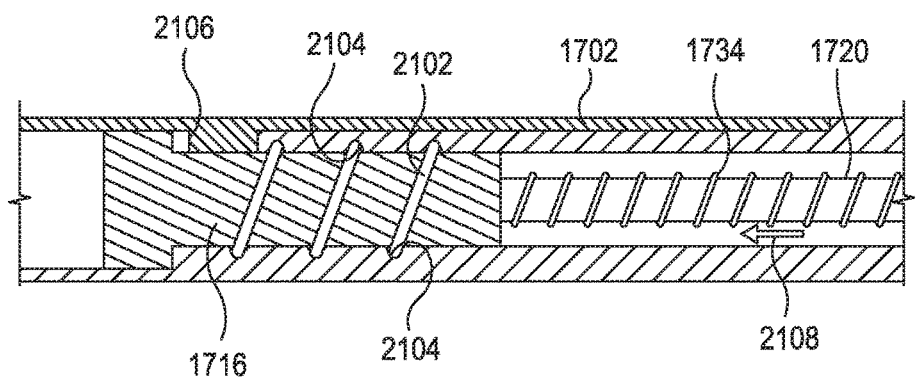

FIGS. 21A-21C illustrate another embodiment of the dispenser 1700 and, more particularly, an alternate method for applying an axial force to the ampoule 1716. In the illustrated embodiment, the ampoule 1716 may define or otherwise provide a series of threads 2102 on its outer surface and may be threaded into internal threads 2104 (FIGS. 21B and 21C) defined on the inner radial surface of the body 1702. The biasing device 1734 may be wound about the plunger 1720 during manufacturing similar to a watch spring. Pushing the ampoule 1716 forward by pressing the activation button 1736 may unlock the ampoule 1716, thereby allowing the biasing device 1734 to unwind. As the biasing device 1734 unwinds, it applies rotational force on the ampoule 1716, which causes the ampoule 1716 to correspondingly move forward as it mates with the internal threads to dispense the dental solution 1726 via the mandrel 1718, as generally described above.

In FIG. 21B, the ampoule 1716 is shown in a locked position in a groove 2106 defined in the body 1702. In FIG. 21C, the ampoule 1716 is depicted as being locked in the groove 2106 to prevent "unwinding" of the biasing device 1734 until the ampoule 1716 is pushed forward in the direction 2108. As will be appreciated, this embodiment may control the rate of dispensing the dental solution 1726 through a combination of spring tension/rate and thread pitch. This may prove advantageous in providing greater leverage over the dental solution 1726 as opposed to embodiments with only the biasing device 1734.

Embodiments disclosed herein include:

A. A dental solution dispenser that includes a body having a first end, a second end opposite the first end, and including a front housing at the first end, a twist back at the second end, and a grip that interposes the front housing and the twist back, an applicator tip coupled to the body at the first end, an ampoule assembly positioned within the body and including an ampoule sealed at one end with a frangible seal and defining a fluid chamber for storing a dental solution, a mandrel extending longitudinally within the body and providing a piercing member, wherein the twist back is rotatable relative to the grip to pierce the frangible seal with the piercing member, and a trigger coupled to the body and pivotable between an engaged position, where the trigger engages the ampoule assembly, and a disengaged position, where the trigger disengages the ampoule assembly.

B. A method of operating a dental solution dispenser that includes rotating a twist back relative to a grip of the dental solution dispenser and thereby moving an ampoule assembly toward a mandrel that provides a piercing member, wherein the ampoule assembly includes an ampoule sealed at one end with a frangible seal and defining a fluid chamber for storing a dental solution, piercing the frangible seal with the piercing member while rotating the twist back relative to a grip, manually manipulating a trigger coupled to the grip and thereby controlling a flow of the dental solution from the fluid chamber to an applicator tip coupled to a front housing of the dental solution dispenser, and discharging the dental solution from the applicator tip.

C. A dental solution dispenser that includes an elongate body having a first end, a second end, and defining an interior that extends between the first and second ends, an applicator tip coupled to the body at the first end, an ampoule positioned within the interior and defining a fluid chamber sealed with a frangible seal and storing a dental solution, a mandrel positioned within the interior and providing a piercing member, an activation button disposed at and extending longitudinally from the second end, wherein actuating the activation button forces the ampoule into contact with the mandrel such that the piercing member penetrates the frangible seal, and a trigger coupled to the body and pivotable between an engaged position, where the trigger engages the ampoule, and a disengaged position, where the trigger disengages the ampoule assembly.

D. A method of operating a dental solution dispenser that includes actuating an activation button extending longitudinally from a second end of a body of a dental solution dispenser, wherein the body defines an interior that extends between a first end and the second end, and an ampoule is positioned within the interior and defines a fluid chamber storing a dental solution and sealed with a frangible seal, piercing the frangible seal with a piercing member of a mandrel positioned within the interior as the activation button is actuated, manually manipulating a trigger coupled to the body and thereby controlling a flow of the dental solution from the fluid chamber to an applicator tip coupled to the first end of the dental solution dispenser, and discharging the dental solution from the applicator tip.

Each of embodiments A, B, C, and D may have one or more of the following additional elements in any combination: Element 1: further comprising a helical slot defined on the twist back, and one or more lugs provided on an inner surface of the grip and matable with the helical slot such that rotation of the twist back relative to the grip draws the twist back into the grip and advances the ampoule assembly toward the piercing member. Element 2: wherein the helical slot provides a variable angular profile. Element 3: further comprising a helical groove defined on an inner surface of the grip, and a helical protrusion defined on the twist back such that rotation of the twist back relative to the grip draws the twist back into the grip and advances the ampoule assembly toward the piercing member. Element 4: further comprising a plunger having a first plunger end and a second plunger end opposite the first plunger end, wherein the ampoule assembly is coupled to the plunger at the second plunger end such that axial movement of the plunger within the body correspondingly moves the ampoule assembly, and a biasing device interposing the first plunger end and an end wall of the twist back, wherein expansion of the biasing device moves the plunger and the ampoule assembly and thereby drives the mandrel into the fluid chamber. Element 5: wherein the first plunger end is threadable with a threaded receptacle defined in the twist back, and wherein rotating the twist back relative to the grip unthreads the first plunger end from the threaded receptacle. Element 6: further comprising a flange provided at the second end of the plunger, and a projection extending radially from the flange and receivable within an axial channel defined on an inner surface of the grip. Element 7: further comprising a stud that extends from the ampoule assembly to couple the ampoule assembly to the plunger. Element 8: further comprising a flange provided at the second end of the plunger and defining at least one groove, and one or more collet fingers extending axially from the twist back and receivable within the at least one groove. Element 9: wherein the trigger provides a catch having an annular body sized to receive the ampoule assembly. Element 10: wherein the mandrel is sized to fit within the fluid chamber and defines a central conduit that fluidly communicates with the applicator tip, and wherein, as the mandrel enters the fluid chamber, the dental solution flows into the central conduit and to the applicator tip.

Element 11: wherein manually manipulating the trigger comprises moving the trigger between an engaged position, where the trigger engages the ampoule assembly, and a disengaged position, where the trigger disengages the ampoule assembly. Element 12: wherein the trigger provides a catch having an annular body sized to receive the ampoule assembly, the method further comprising engaging the catch on the ampoule assembly with the trigger in the engaged position, and disengaging the catch from the ampoule assembly with the trigger in the disengaged position. Element 13: wherein the twist back defines a helical slot matable with one or more lugs provided on an inner surface of the grip, and wherein rotating the twist back relative to the grip comprises receiving the one or more lugs within the helical slot, and progressively drawing a portion of the twist back into the grip as the one or more lugs translate within the helical slot. Element 14: wherein the twist back defines a helical protrusion matable with a helical groove defined on an inner surface of the grip, and wherein rotating the twist back relative to the grip comprises receiving the helical protrusion within the helical groove, and progressively drawing a portion of the twist back into the grip as the helical protrusion translates within the helical groove. Element 15: wherein the dental solution dispenser further includes a plunger that defines a flange and is coupled to the ampoule assembly, and wherein rotating the twist back relative to the grip further comprises receiving a projection extending radially from the flange within an axial channel defined on an inner surface of the grip and thereby preventing the plunger from correspondingly rotating relative to the grip, unthreading the plunger from a threaded receptacle provided in the twist back as the twist back rotates relative to the grip, and driving the mandrel into the fluid chamber under force of a biasing device interposing the flange and an end wall of the twist back once the plunger unthreads from the threaded receptacle. Element 16: wherein the dental solution dispenser further includes a plunger coupled to the ampoule assembly, a flange defined on the plunger and defining at least one groove, and one or more collet fingers extending axially from the twist back and receivable within the at least one groove, and wherein rotating the twist back relative to the grip further comprises advancing the plunger into the grip and maintaining the one or more collet fingers in radial engagement with the at least one groove while positioned axially within a first inner diameter of the grip, and disengaging the one or more collet fingers from the at least one groove once positioned axially within a second inner diameter of the grip, wherein the second inner diameter exhibits a diameter greater than the first inner diameter. Element 17: wherein piercing the frangible seal with the piercing member comprises piercing the frangible seal while the ampoule rotates. Element 18: wherein discharging the dental solution from the applicator tip comprises advancing the mandrel into the fluid chamber, flowing the dental solution into a central conduit of the mandrel and to a delivery conduit of the applicator tip as the mandrel advances into the fluid chamber, and applying the dental solution to a surface of a tooth with a brush applicator of the applicator tip.

Element 19: further comprising a biasing device interposing the ampoule and an end wall defined in the interior at the second end, wherein expansion of the biasing device moves the ampoule such that the mandrel extends into the fluid chamber. Element 20: further comprising a plunger that interposes the ampoule and the second end. Element 21: wherein the activation button comprises an axial extension of the plunger. Element 22: wherein the trigger comprises a catch that engages the ampoule when the trigger is in the engaged position and disengages the ampoule when the trigger is in the disengaged position. Element 23: wherein the catch generates friction against an outer surface of the ampoule to slow or stop movement of the ampoule toward the mandrel. Element 24: further comprising a plurality of ridges defined on an outer surface of the ampoule, wherein the catch engages the plurality of ridges when the trigger is in the engaged position. Element 25: wherein the mandrel is coupled to and extends from the applicator tip.

Element 26: wherein a biasing device interposes the ampoule and an end wall defined in the interior at the second end, the method further comprising expanding the biasing device and thereby moving the ampoule within the interior such that the mandrel extends into the fluid chamber. Element 27: wherein the mandrel is sized to fit within the fluid chamber and the method further comprises generating a hydraulic seal between an inner wall of the fluid chamber and an outer wall of the mandrel as the mandrel extends into the fluid chamber. Element 28: wherein actuating the activation button comprises manually pressing the activation button, and forcing a plunger that interposes the ampoule and the second end into axial engagement with the ampoule. Element 29: wherein manually manipulating the trigger comprises moving the trigger between an engaged position, where the trigger engages the ampoule, and a disengaged position, where the trigger disengages the ampoule. Element 30: wherein the trigger provides a catch engageable with an outer surface of the ampoule, the method further comprising engaging the catch on the outer surface of the ampoule with the trigger in the engaged position, and disengaging the catch from the outer surface of the ampoule with the trigger in the disengaged position. Element 31: wherein engaging the catch on the outer surface of the ampoule comprises engaging the catch on a plurality of ridges defined on an outer surface of the ampoule. Element 32: wherein discharging the dental solution from the applicator tip comprises advancing the mandrel into the fluid chamber, flowing the dental solution into a central conduit of the mandrel and to a delivery conduit of the applicator tip as the mandrel advances into the fluid chamber, and applying the dental solution to a surface of a tooth with a brush applicator of the applicator tip.

By way of non-limiting example, exemplary combinations applicable to A, B, and C include: Element 1 with Element 2; Element 4 with Element 5; Element 4 with Element 6; Element 4 with Element 7; Element 4 with Element 8; Element 11 with Element 12; Element 20 with Element 21; Element 22 with Element 23; Element 22 with Element 24; Element 26 with Element 27; and Element 29 with Element 30.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A dental solution dispenser, comprising: a body having a first end and a second end opposite the first end, a front housing at the first end, a twist back at the second end; an applicator tip coupled to the body at the first end; the body configured to receive an ampoule assembly positioned within the body, the ampoule assembly including an ampoule sealed at one end with a frangible seal and defining a fluid chamber for storing a dental solution; a mandrel extending longitudinally within the body and providing a piercing member, wherein the twist back is rotatable relative to the body to pierce the frangible seal with the piercing member; and a trigger coupled to the body, wherein the trigger comprises a catch having an annular body sized to receive the ampoule assembly, and pivotable between an engage position, where the annular body is configured to engage the ampoule assembly, and a disengaged position, where the annular body is configured to disengage the ampoule assembly.

2. The dental solution dispenser of claim 1, further comprising:
   a helical slot defined on the twist back; and
   one or more lugs provided on an inner surface of the body and matable with the helical slot such that rotation of the twist back relative to the body draws the twist back into the body and advances the ampoule assembly toward the piercing member.

3. The dental solution dispenser of claim 2, wherein the helical slot provides a variable angular profile.

4. The dental solution dispenser of claim 1, further comprising:
   a helical groove defined on an inner surface of the grip; and
   a helical protrusion defined on the twist back such that rotation of the twist back relative to the grip draws the twist back into the grip and advances the ampoule assembly toward the piercing member.

5. The dental solution dispenser of claim 1, further comprising:
   a plunger having a first plunger end and a second plunger end opposite the first plunger end, wherein the ampoule assembly is coupled to the plunger at the second plunger end such that axial movement of the plunger within the body correspondingly moves the ampoule assembly; and
   a biasing device interposing the first plunger end and an end wall of the twist back, wherein expansion of the biasing device moves the plunger and the ampoule assembly and thereby drives the mandrel into the fluid chamber.

6. The dental solution dispenser of claim 5, wherein the first plunger end is threadable with a threaded receptacle defined in the twist back, and wherein rotating the twist back relative to the body unthreads the first plunger end from the threaded receptacle.

7. The dental solution dispenser of claim 5, further comprising:
   a flange provided at the second end of the plunger; and
   a projection extending radially from the flange and receivable within an axial channel defined on an inner surface of the body.

8. The dental solution dispenser of claim 5, further comprising a stud that extends from the ampoule assembly to couple the ampoule assembly to the plunger.

9. The dental solution dispenser of claim 5, further comprising:
   a flange provided at the second end of the plunger and defining at least one groove; and
   one or more collet fingers extending axially from the twist back and receivable within the at least one groove.

10. The dental solution dispenser of claim 1, wherein the mandrel is sized to fit within the fluid chamber and defines a central conduit that fluidly communicates with the applicator tip, and wherein, as the mandrel enters the fluid chamber, the dental solution flows into the central conduit and to the applicator tip.

11. The dental solution dispenser of claim 1, wherein the mandrel is sized to fit within the fluid chamber and defines a central conduit that fluidly communicates with the applicator tip, and wherein, as the mandrel enters the fluid chamber, the dental solution flows into the central conduit and to the applicator tip.

12. A dental solution dispenser, comprising; a body comprising; a first end, a second end opposite the first end, a front housing extending from the body first end, a twist back configured to rotatably connect to the body second end and containing a threaded receptacle defined to receive a plunger; an applicator tip coupled to the body at the first end; the body configured to receive an ampoule assembly, the ampoule assembly including an ampoule sealed at one end with a frangible seal and defining a fluid chamber for storing a dental solution; a mandrel within the body, the mandrel including a piercing member; and a plunger having a first plunger end and a second plunger end opposite the first plunger end, the first plunger end is threadable with the threaded receptacle defined in the twist back, and wherein rotating the twist back relative to the body unthreads and disengages the first plunger end from the thread receptacle; wherein axial movement of the plunger within the body correspondingly moves the ampoule assembly, and a trigger coupled to the body, wherein the trigger comprises a catch having an annular body sized to receive the ampoule assembly, and pivotable between an engage position, where the annular body is configured to engage the ampoule assembly, and a disengaged position, where the annular body is configured to disengage the ampoule assembly.

13. The dental solution dispenser of claim 12, further comprising:
   a helical slot defined on the twist back; and
   one or more lugs provided on an inner surface of the body and matable with the helical slot such that rotation of the twist back relative to the body draws the twist back into the body and advances the ampoule assembly toward the piercing member.

14. The dental solution dispenser of claim 13, wherein the helical slot provides a variable angular profile.

15. The dental solution dispenser of claim 12 further comprising a biasing device interposing the first plunger end and an end wall of the twist back, wherein expansion of the biasing device moves the plunger and the ampoule assembly and thereby drives the mandrel into the fluid chamber.

16. The dental solution dispenser of claim 12, further comprising:
   a flange provided at the second end of the plunger; and
   a projection extending radially from the flange and receivable within an axial channel defined on an inner surface of the body.

17. The dental solution dispenser of claim 12, further comprising a stud that extends from the ampoule assembly to couple the ampoule assembly to the plunger.

18. The dental solution dispenser of claim 12, further comprising:
   a flange provided at the second end of the plunger and defining at least one groove; and
   one or more collet fingers extending axially from the twist back and receivable within the at least one groove.

19. A dental solution dispenser, comprising: an elongated body having a first end, a second end, and defining an interior that extends between the first and second ends; an applicator tip coupled to the body at the first end; the elongated body configured to receive an ampoule positioned within the interior; a mandrel positioned within the interior and providing a piercing member; a biasing device interposing the ampoule and an end wall defined in the interior at the second end, wherein the biasing device is configured to bias the ampoule toward the mandrel; and a trigger coupled to the body, wherein the trigger comprises a catch having an annular body sized to receive the ampoule assembly, and pivotable between: an engaged position configured to engage the annular body with the ampoule to impede movement of the ampoule, and a disengaged position configured to disengage the annular body from the ampoule.

20. The dental solution dispenser of claim 19, further comprising a plunger that interposes the ampoule and the second end.

21. The dental solution dispenser of claim 19, wherein the catch engages the ampoule when the trigger is in the engaged position and disengages the ampoule when the trigger is in the disengaged position.

22. The dental solution dispenser of claim 19, wherein the catch generates friction against an outer surface of the ampoule to slow or stop movement of the ampoule toward the mandrel.

23. The dental solution dispenser of claim 19, further comprising a plurality of ridges defined on an outer surface of the ampoule, wherein the catch engages the plurality of ridges when the trigger is in the engaged position.

24. The dental solution dispenser of claim 19, wherein the mandrel is coupled to and extends from the applicator tip.

\* \* \* \* \*